(12) United States Patent
Peoples et al.

(10) Patent No.: US 9,114,099 B2
(45) Date of Patent: Aug. 25, 2015

(54) VACCINE FOR THE PREVENTION OF BREAST CANCER RECURRENCE

(75) Inventors: George Peoples, San Antonio, TX (US); Sathibalan Ponniah, Columbia, MD (US)

(73) Assignee: The Henry M. Jackson Foundation for the Advancement of Miltary Medicine, Inc., Bethesda, MD (US)

( * ) Notice: Subject to any disclaimer, the term of this patent is extended or adjusted under 35 U.S.C. 154(b) by 988 days.

(21) Appl. No.: 13/133,487

(22) PCT Filed: Dec. 9, 2009

(86) PCT No.: PCT/US2009/067264
§ 371 (c)(1),
(2), (4) Date: Jun. 8, 2011

(87) PCT Pub. No.: WO2010/068647
PCT Pub. Date: Jun. 17, 2010

(65) Prior Publication Data
US 2011/0256164 A1 Oct. 20, 2011

Related U.S. Application Data

(60) Provisional application No. 61/121,220, filed on Dec. 10, 2008.

(51) Int. Cl.
*A61K 38/00* (2006.01)
*C07K 7/06* (2006.01)
*C07K 14/00* (2006.01)
*A61K 39/00* (2006.01)

(52) U.S. Cl.
CPC ... *A61K 39/0011* (2013.01); *A61K 2039/55522* (2013.01)

(58) Field of Classification Search
CPC ........... A61K 38/00; C07K 7/06; C07K 14/00
USPC ................................ 424/185.1; 530/328, 350
See application file for complete search history.

(56) References Cited

U.S. PATENT DOCUMENTS

| | | | |
|---|---|---|---|
| 5,550,214 | A | 8/1996 | Eberlein et al. |
| 5,726,023 | A | 3/1998 | Cheever et al. |
| 6,482,407 | B2 * | 11/2002 | Soo Hoo .................... 424/93.21 |
| 7,211,432 | B2 | 5/2007 | Schlom et al. |
| 7,446,185 | B2 | 11/2008 | Nelson |
| 2004/0018971 | A1 | 1/2004 | Fikes et al. |
| 2008/0260745 | A1 | 10/2008 | Ponniah et al. |
| 2011/0256164 | A1 | 10/2011 | Peoples |

FOREIGN PATENT DOCUMENTS

WO 2008150577 12/2008

OTHER PUBLICATIONS

Peoples et al. (J Clin Oncol, 2005, 23: 7536-7545).*
NCBI MeSH—Granulocyte-Macrophage Colony-Stimulating Factor.*
English Translation of the Text of the First Office Action issued in Chinese Patent Application No. 200980149404.7 dated Dec. 23, 2012, 4 pages.
Amin, Asna et al. Assessment of immunologic response and recurrence patterns among patients with clinical recurrence after vaccination with a preventive HER2/neu peptide vaccine: from US Military Cancer Institute Clinical Trials Group Study I-01 and I-02. Cancer Immunol. Ummunother (2008) 57:1817-1825.
Carmichael, Mark G. et al. Breast Cancer Research Treatment. 30th Annual San Antonio Breast Cancer Symposium, Dec. 2007, vol. 106, Supplement 1, pp. S30-S31.
European Patent Office Communication issued in European Patent Application No. 09832462.7 dated Mar. 14, 2013, 9 pages.
Peoples, G. E. HER2/neu Vaccines for Cancer. Nov. 16, 2007, 58 pages, XP002691920, Retrieved from http://www.esmo.org/fileadmin/media/presentations/826/LCT10001553.pdf.
Anonymous. Selected Clinical Trials in Breast Cancer. Clinical Breast Cancer, Oct. 1, 2007, pp. 814-815, XP002691921. Retrieved from http://cigjournals.metapress.com/content/8438658656p49310/fulltext.pdf.
Mittendorf et al. Vaccination with a HER2/neu peptide induces intra- and inter-antigenic epitope spreading in patients with early stage breat cancer. Surgery, vol. 130, No. 3. Mar. 1, 2006, pp. 407-418, XP005338910.
Mittendorf et al. HER-2/neu Peptide Breast Cancer Vaccines: Current Status and Future Directions. Breast Diseases: A Year Book Quarterly, vol. 17, No. 4, Jan. 1, 2007, pp. 318-320, XP022090171.
Mittendorf, Elizabeth A et al. The E75 HER2/neu peptide vaccine. Cancer Immunology Immunotherapy, vol. 57, No. 10, Jun. 7, 2008, pp. 1511-1521, XP019624429.
Mittendorf, Elizabeth A et al, Evaluation of the HER2/neu-Derived Peptide GP2 for Use in a Peptide-Based Breast Cancer Vaccine Trial. Cancer, vol. 106, Jan. 1, 2006, pp. 2309-2317, XP007910301.

(Continued)

*Primary Examiner* — Yan Xiao
(74) *Attorney, Agent, or Firm* — MH2 Technology Law Group, LLP

(57) ABSTRACT

Provided are methods to induce and maintain a protective cytotoxic T-lymphocyte response to a peptide of the HER/neu oncogene, GP2, with the effect of inducing and maintaining protective or therapeutic immunity against breast cancer in a patient in clinical remission, including patients having low to intermediate levels of HER2/neu expression. The methods comprise administering to the patient an effective amount of a vaccine composition comprising a pharmaceutically acceptable carrier, an adjuvant such as GM-CSF, and the GP2 peptide. The methods may further comprise administering a periodic booster vaccine dose as needed due to declining GP2-specific T cell immunity. Also provided are vaccine compositions for use in the methods.

16 Claims, 6 Drawing Sheets

(56) References Cited

OTHER PUBLICATIONS

Holmes, J P et al, Intra-antigenic epitope spreading in HLA-A2+breast cancer patients vaccinated with a MHC class I peptide (GP2) derived from the transmembrane region of HER2/NEU. Journal of Immunotherapy, vol. 30, No, 8, Nov. 4, 2007, XP009166967.
Mittendorf et al. (Proc. Amer. Assoc. Cancer Research, Apr. 2005, 46:abstract#3449).
Mittendorf et al., Journal of the American College of Surgeons, vol. 203, No. 3 (Sep. 2006), pp. S79.
Tanaka et al., International Journal of Cancer, vol. 94, No. 4 (Nov. 2001), pp. 540-544.
Mittendorf et al., Breast Diseases: A Year Book Quaterly, vol. 17, No. 4 (Jan. 2007), pp. 318-320.
Knutson, Keith L. et al. Immunization of Cancer Patients with a HER-2/neu, HLA-A2 Peptide, p. 369-377, Results in Short-lived Peptide-specific Immunity. Clinical Cancer Research, May 2002, vol. 8, pp. 1014-1018.
Bernhard, H. et al. Vaccination against the HER-2/neu oncogenic protein, Endocrine-Related Cancer, 2002, vol. 9, pp. 33-44.
Carmichael, Mark G. et al. Results of the First Phase 1 Clinical Trial of the HER-2/neu Peptide (GP2) Vaccine in Disease-Free Breast Cancer Patients. Cancer, Jan. 15, 2010, pp. 292-301.
Vaccine Therapy in Treating Patients With Stage IV Breast Cancer. ClinicalTrials.gov, pp. 1-4, http://clinicaltrials.gov/show/NCT00791037, first received Nov. 13, 2008, last updated Sep. 16, 2013, printed Sep. 15, 2014.

\* cited by examiner

SEQUENCE LISTING

```
<160> NUMBER OF SEQ ID NOS: 5

<210> SEQ ID NO 1
<211> LENGTH: 1225
<212> TYPE: PRT
<213> ORGANISM: Homo sapiens

<400> SEQUENCE: 1

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140
```

-continued

```
Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
            165                 170                 175

Glu Ser Ser Glu Asp Cys Gln Ser Leu Thr Arg Thr Val Cys Ala Gly
        180                 185                 190

Gly Cys Ala Arg Cys Lys Gly Pro Leu Pro Thr Asp Cys Cys His Glu
    195                 200                 205

Gln Cys Ala Ala Gly Cys Thr Gly Pro Lys His Ser Asp Cys Leu Ala
210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
```

```
                565                 570                 575
Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
            595                 600                 605

Asp Lys Gly Cys Pro Ala Glu Gln Arg Ala Ser Pro Leu Thr Ser Ile
        610                 615                 620

Ile Ser Ala Val Val Gly Ile Leu Leu Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990
```

-continued

```
Tyr Leu Val Pro Gln Gln Gly Phe  Phe Cys Pro Asp Pro  Ala Pro Gly
        995                 1000                 1005

Ala Gly  Gly Met Val His  His  Arg His Arg Ser  Ser  Ser Thr Arg
    1010             1015                 1020

Ser Gly  Gly Gly Asp Leu  Thr  Leu Gly Leu Glu  Pro  Ser Glu Glu
    1025             1030                 1035

Glu Ala  Pro Arg Ser Pro  Leu  Ala Pro Ser Glu  Gly  Ala Gly Ser
    1040             1045                 1050

Asp Val  Phe Asp Gly Asp  Leu  Gly Met Gly Ala  Ala  Lys Gly Leu
    1055             1060                 1065

Gln Ser  Leu Pro Thr His  Asp  Pro Ser Pro Leu  Gln  Arg Tyr Ser
    1070             1075                 1080

Glu Asp  Pro Thr Val Pro  Leu  Pro Ser Glu Thr  Asp  Gly Tyr Val
    1085             1090                 1095

Ala Pro  Leu Thr Cys Ser  Pro  Gln Pro Glu Tyr  Val  Asn Gln Pro
    1100             1105                 1110

Asp Val  Arg Pro Gln Pro  Pro  Ser Pro Arg Glu  Gly  Pro Leu Pro
    1115             1120                 1125

Ala Ala  Arg Pro Ala Gly  Ala  Thr Leu Glu Arg  Pro  Lys Thr Leu
    1130             1135                 1140

Ser Pro  Gly Lys Asn Gly  Val  Val Lys Asp Val  Phe  Ala Phe Gly
    1145             1150                 1155

Gly Ala  Val Glu Asn Pro  Glu  Tyr Leu Thr Pro  Gln  Gly Gly Ala
    1160             1165                 1170

Ala Pro  Gln Pro His Pro  Pro  Pro Ala Phe Ser  Pro  Ala Phe Asp
    1175             1180                 1185

Asn Leu  Tyr Tyr Trp Asp  Gln  Asp Pro Pro Glu  Arg  Gly Ala Pro
    1190             1195                 1200

Pro Ser  Thr Phe Lys Gly  Thr  Pro Thr Ala Glu  Asn  Pro Glu Tyr
    1205             1210                 1215

Leu Gly  Leu Asp Val Pro  Val
    1220             1225

<210> SEQ ID NO 2
<211> LENGTH: 9
<212> TYPE: PRT
<213> ORGANISM: Homo sapiens

<400> SEQUENCE: 2

Ile Ile Ser Ala Val Val Gly Ile Leu
1               5

<210> SEQ ID NO 3
<211> LENGTH: 9
<212> TYPE: PRT
<213> ORGANISM: Homo sapiens

<400> SEQUENCE: 3

Lys Ile Phe Gly Ser Leu Ala Phe Leu
1               5

<210> SEQ ID NO 4
<211> LENGTH: 9
<212> TYPE: PRT
<213> ORGANISM: Homo sapiens

<400> SEQUENCE: 4
```

```
Ile Val Ser Ala Val Val Gly Ile Leu
1               5

<210> SEQ ID NO 5
<211> LENGTH: 9
<212> TYPE: PRT
<213> ORGANISM: Homo sapiens

<400> SEQUENCE: 5

Arg Ile Ala Trp Ala Arg Thr Glu Leu
1               5
```

VACCINE FOR THE PREVENTION OF BREAST CANCER RECURRENCE

CROSS REFERENCE TO RELATED APPLICATIONS

This is the U.S. National Phase application of International Application PCT/US2009/067264, filed 9 Dec. 2009, which claims the benefit of, and relies on the filing date of, U.S. provisional application No. 61/121,220, filed 10 Dec. 2008, the entire disclosure of which is incorporated herein by reference.

GOVERNMENT INTEREST

This invention was made in part with Government support. The Government may have certain rights in the invention.

SEQUENCE LISTING

The instant application contains a Sequence Listing, which has been submitted via EFS-Web and is hereby incorporated by reference in its entirety. Said ASCII copy, created on 7 Dec. 2009, is named HMJ106PCT.txt, and is 11,473 bytes in size.

BACKGROUND

Breast cancer (BCa) is the most common cancer diagnosis in women and the second-leading cause of cancer-related death among women (Ries L A G, et al. (eds). SEER Cancer Statistics Review, 1975-2003, National Cancer Institute, Bethesda, Md.). Major advances in breast cancer treatment over the last 20 years have led to significant improvement in the rate of disease-free survival (DFS). For example, therapies utilizing antibodies reactive against tumor-related antigens have been used to block specific cellular processes in order to slow disease progress or prevent disease recurrence. Despite the recent advances in breast cancer treatment, a significant number of patients will ultimately die from recurrent disease.

Vaccines are an attractive model for preventing, slowing, or prohibiting the development of recurrent disease due to their ease of administration, and because of their high rate of success observed for infectious diseases. The basic concept of constructing a cancer vaccine is straightforward in theory. The development of effective cancer vaccines for solid tumors in practice, however, has met with limited success. For example, one group attempting to administer a peptide vaccine directed against metastatic melanoma observed an objective response rate of only 2.6% (Rosenberg S A et al. (2004) Nat. Med. 10:909-15).

There are many potential explanations for this low success rate (Campoli M et al. (2005) Cancer Treat. Res. 123:61-88). For example, even if an antigen is specifically associated with a particular type of tumor cell, the tumor cells may express only low levels of the antigen, or it may be located in a cryptic site or otherwise shielded from immune detection. In addition, tumors often change their antigenic profile by shedding antigens as they develop. Also contributing to the low success rate is the fact that tumor cells may express very low levels of MHC proteins and other co-stimulatory proteins necessary to generate an immune response.

Additional problems facing attempts at vaccination against tumors arise in patients with advanced-stage cancers. Such patients tend to have larger primary and metastatic tumors, and the cells on the interior of the tumor may not be accessible due to poor blood flow. This is consistent with the observation that vaccine strategies have tended to be more successful for the treatment of hematologic malignancies (Radford K J et al. (2005) Pathology 37:534-50; and, Molldrem J J (2006) Biol. Bone Marrow Transplant. 12:13-8). In addition, as tumors become metastatic, they may develop the ability to release immunosuppressive factors into their microenvironment (Campoli, 2005; and, Kortylewski M et al. (2005) Nature Med. 11:1314-21). Metastatic tumors have also been associated with a decrease in the number of peripheral blood lymphocytes, and dendritic cell dysfunction (Gillanders W E et al. (2006) Breast Diseases: A Year Book and Quarterly 17:26-8).

While some or all of these factors may contribute to the difficulty in developing an effective preventative or therapeutic vaccine, the major underlying challenge is that most tumor antigens are self antigens or have a high degree of homology with self antigens, and are thus expected to be subject to stringent immune tolerance. Thus, it is clear that many peptide-based cancer vaccines, with or without immune-stimulating adjuncts, may be doomed to only limited success in clinical practice due to low immunogenicity and lack of specificity.

Prototype breast cancer vaccines based on single antigens have been moderately successful in inducing a measurable immune response in animal experiments and in clinical tests with breast cancer patients. The observed immune response, however, has not translated into a clinically-significant protective immunity against recurrence of disease put in remission by standard therapy (e.g., surgery, radiation therapy, and chemotherapy).

HER2/neu is a proto-oncogene expressed in many epithelial malignancies (Slamon D J et al. (1989) Science 244:707-12). HER2/neu is a member of the epidermal growth factor receptor family and encodes a 185-kd tyrosine kinase receptor involved in regulating cell growth and proliferation. (Popescu N C et al. (1989) Genomics 4:362-366; Yarden Y et al. (2001) Nat Rev Mol Cell Bio 2:127-137.) Over-expression and/or amplification of HER2/neu is found in 25-30% of invasive breast cancers (BCa) and is associated with more aggressive tumors and a poorer clinical outcome. (Slamon D J et al. Science (1987) 235:177-182; Slamon D J et al. Science (1989) 244:707-12; Toikkanen S et al. J Clin Oncol (1992) 10:1044-1048; Pritchard K I et al. (2006) N. Engl. J. Med. 354:2103-11.)

Determining HER2/neu status is performed predominately via two tests, immunohistochemistry (IHC) and fluorescence in situ hybridization (FISH). IHC detects over-expression of HER2/neu protein and is reported on a semi-quantitative scale of 0 to 3+ ($0=$negative, $1^+=$low expression, $2^+=$intermediate, and $3^+=$over-expression). FISH on the other hand detects amplification (excess copies) of the HER2/neu gene and is expressed as a ratio of HER2/neu gene copies to chromosome 17 gene copies and interpreted as "over-expression" if FISH is ≥2.0 copies. (Hicks D G et al. Hum Pathol (2005) 36:250-261.) Concurrence rate of IHC and FISH is approximately 90%. (Jacobs et al. J Clin Oncol (1999) 17:1533-1541.) FISH is considered the gold standard, as retrospective analysis reveals it is a better predictor of trastuzumab (Tz) response; it is more objective and reproducible. (Press M F et al. J Clin Oncol (2002) 14:3095-3105; Bartlett J et al. J Pathol (2003) 199:411-417; Wolff A C et al. J Clin Oncol (2007) 25:118-145.)

Identification and quantification of HER2/neu as a proto-oncogene has led to humoral or antibody-based passive immunotherapy, including the use of trastuzumab (Herceptin® Genentech Inc., South San Francisco, Calif.). Trastuzumab is a recombinant, humanized monoclonal antibody that binds the extracellular juxtamembrane domain of HER2/neu protein. (Plosker G L et al. Drugs (2006) 66:449-475.) Tz is indicated for HER2/neu over-expressing (IHC 3$^+$ or FISH≥2.0) node-positive (NP) and metastatic BCa patients, (Vogel C L et al. J Clin Oncol (2002) 20:719-726; Piccart-Gebhart M J et al. N Engl J Med (2005) 353:1659-1672) and shows very limited activity in patients with low to intermediate HER2/neu expression. (Herceptin® (Trastuzumab), prescription product insert, Genentech Inc, South San Francisco, Calif.: revised September 2000.)

Another form of immunotherapy being pursued is vaccination and active immunotherapy targeting a cellular immune response to epitopes on tumor associated antigens, such as HER2/neu. HER2/neu is a source of several immunogenic peptides that can stimulate the immune system to recognize and kill HER2/neu-expressing cancer cells. (Fisk B et al. J Exp Med (1995) 181:2109-2117.) Two such peptides are termed E75 and GP2. E75 and GP2 are both nine amino-acid peptides that are human leukocyte antigen (HLA)-A2-restricted and stimulate CTL to recognize and lyse HER2/neu-expressing cancer cells (Fisk B et al. J Exp Med (1995) 181:2109-2117; Peoples G E et al. Proc Natl Acad Sci USA (1995) 92:432-436).

E75 is derived from the extracellular domain of the HER2/neu protein and corresponds to amino acids 369-377 (KIFGSLAFL) (SEQ ID NO:3) of the HER2/neu amino acid sequence and is disclosed as SEQ ID NO:11 in U.S. Pat. No. 6,514,942, which patent is hereby incorporated by reference in its entirety. The full length HER2/neu protein sequence is set forth below and is disclosed as SEQ ID NO:2 in U.S. Pat. No. 5,869,445, which patent is hereby incorporated by reference in its entirety:

```
                                              (SEQ ID NO: 1)
MKLRLPASPETHLDMLRHLYQGCQVVQGNLELTYLPTNASLSFL

QDIQEVQGYVLIAHNQVRQVPLQRLRIVRGTQLFEDNYALAVLDNGDPLN

NTTPVTGASPGGLRELQLRSLTEILKGGVLIQRNPQLCYQDTILWKDIFH

KNNQLALTLIDTNRSRACHPCSPMCKGSRCWGESSEDCQSLTRTVCAGGC

ARCKGPLPTDCCHEQCAAGCTGPKHSDCLACLHFNHSGICELHCPALVTY

NTDTFESMPNPEGRYTFGASCVTACPYNYLSTDVGSCTLVCPLHNQEVTA

EDGTQRCEKCSKPCARVCYGLGMEHLREVRAVTSANIQEFAGCKKIFGSL

AFLPESFDGDPASNTAPLQPEQLQVFETLEEITGYLYISAWPDSLPDLSV

FQNLQVIRGRILHNGAYSLTLQGLGISWLGLRSLRELGSGLALIHHNTHL

CFVHTVPWDQLFRNPHQALLHTANRPEDECVGEGLACHQLCARGHCWGPG

PTQCVNCSQFLRGQECVEECRVLQGLPREYVNARHCLPCHPECQPQNGSV

TCFGPEADQCVACAHYKDPPFCVARCPSGVKPDLSYMPIWKFPDEEGACQ

PCPINCTHSCVDLDDKGCPAEQRASPLTSIISAVVGILLVVVLGVVFGIL

IKRRQQKIRKYTMRRLLQETELVEPLTPSGAMPNQAQMRILKETELRKVK

VLGSGAFGTVYKGIWIPDGENVKIPVAIKVLRENTSPKANKEILDEAYVM

AGVGSPYVSRLLGICLTSTVQLVTQLMPYGCLLDHVRENRGRLGSQDLLN

WCMQIAKGMSYLEDVRLVHRDLAARNVLVKSPNHVKITDFGLARLLDIDE

TEYHADGGKVPIKWMALESILRRRFTHQSDVWSYGVTVWELMTFGAKPYD

GIPAREIPDLLEKGERLPQPPICTIDVYMIMVKCWMIDSECRPRFRELVS
```

```
EFSRMARDPQRFVVIQNEDLGPASPLDSTFYRSLLEDDDMGDLVDAEEYL

VPQQGFFCPDPAPGAGGMVHHRHRSSSTRSGGGDLTLGLEPSEEEAPRSP

LAPSEGAGSDVFDGDLGMGAAKGLQSLPTHDPSPLQRYSEDPTVPLPSET

DGYVAPLTCSPQPEYVNQPDVRPQPPSPREGPLPAARPAGATLERPKTLS

PGKNGVVKDVFAFGGAVENPEYLTPQGGAAPQPHPPPAFSPAFDNLYYWD

QDPPERGAPPSTFKGTPTAENPEYLGLDVPV
```

Attempts have been made to utilize E75 as an anti-cancer vaccine, for example, as a single peptide vaccine combined with different immunoadjuvants in patients with advanced cancer who overexpress the HER2/neu protein (Zaks T Z et al. (1998) Cancer Res. 58:4902-8; Knutson K L et al. (2002) Clin. Cancer Res. 8:1014-8; and, Murray J L et al. (2002) Clin. Cancer Res. 8:3407-18); loaded on to autologous dendritic cells and reinfused (Brossart P et al. (2000) Blood 96:3102-8; and, Kono K et al. (2002) Clin. Cancer Res. 8:3394-3400); or embedded in longer peptides capable of binding HLA class II molecules in order to recruit CD4 helper T-cells (Disis M L et al. (1999) Clin. Cancer Res. 5:1289-97; and, Disis M L et al. (2002) J. Clin. Oncol. 20:2624-32). Each approach has stimulated an E75-specific cytotoxic T cell-mediated immune response, but none has demonstrated a clinically significant therapeutic or protective immunity in women with advanced stage breast cancer. The inability of others to show a meaningful clinical benefit using E75 vaccine preparations stems in part from the fact that E75 is derived from a "self" tumor antigen. Cancer vaccines targeting "self" tumor antigens, like those derived from HER2/neu, present unique challenges because of the immunologic tolerance characteristic of self proteins. Furthermore, the previous studies have focused on cancer patients with advanced disease, such as Stage III or IV cancer, rather than patients who are disease-free following standard therapies. As such, none of these attempts to use E75 as an anti-cancer vaccine has demonstrated the vaccine's ability to prevent or delay recurrence of disease following remission. Building on these E75 studies, others have more recently conducted clinical trials to determine if E75-induced immunity conveys a clinical benefit by preventing the recurrence in high-risk breast cancer patients. Peoples G E et al., J. Clin. Oncol. (2005) 23:7536-45; Peoples G E et al., Clin Cancer Res (2008) 14(3):797-803; Holmes et al., Cancer (2008) 113:1666-75. The data from these studies indicate that increased in vivo E75-induced DTH responses correlate with reduced recurrence and increased survival time for those who did recur.

GP2, initially described by Peoples et al., is a nine amino acid peptide derived from the transmembrane portion of the HER2/neu protein corresponding to amino acids 654-662 of the full length sequence (i.e., IISAVVGIL: SEQ ID NO:2) (Peoples G E et al., Proc Natl Acad Sci USA (1995) 92:432-436, which is hereby incorporated by reference in its entirety). The peptide was isolated using tumor-associated lymphocytes from patients with breast and ovarian cancer, and later found to be shared amongst several epithelial malignancies including non-small cell lung cancer and pancreatic cancer (Linehan D C et al., J Immunol (1995) 155:4486-4491; Peiper M et al., Surgery (1997) 122:235-242; Yoshino I et al., Cancer Res (1994) 54:3387-3390; Peiper M et al., Eur J Immunol (1997) 27:1115-1123).

E75 has a high binding affinity for the HLA-A2 molecule and is considered the immunodominant peptide of the HER2/neu protein. As such it is the most studied HER2/neu-derived peptide in laboratory and clinical studies. Peoples et al., J. Clin. Oncol. (2005) 23:7536-45. As the immunodominant peptide, E75 is also expected to induce a more potent immune response. GP2, on the other hand, has a relatively poor binding affinity to HLA-A2 and is considered a subdominant epitope. (Fisk B, et al. J Exp Med (1995) 181:2109-2117.) This is one of the reasons that vaccine strategies targeting a cellular immune response to HER-2/neu epitopes have focused on E75 rather than GP2.

Previous studies of GP2 have used autologous dendritic cells pulsed with GP2 (and other peptides) ex vivo and re-injected subcutaneously (Brossart P et al. Blood (2000) 96:3102-3108) or intravenously (Dees E C et al. Cancer Immunol Immunother (2004) 53:777-785) into HER2/neu+ patients with metastatic breast or ovarian cancer to induce a CTL response. Brossart et al. detected a peptide-specific (GP2 and E75) CTL response in vivo, and they noted that both peptides showed a similar immune response despite known differences in HLA-A2 binding affinities. Dees et al. evaluated GP2-pulsed dendritic cells in metastatic breast cancer patients and were able to document clinically stable disease in two patients. Importantly, however, neither study used GP2 as a peptide vaccine. Rather in both studies, patients were injected with dendritic cells that had been pulsed with GP2. Furthermore, as with the E75 studies, the GP2 studies were limited to patients with advanced cancer. Therefore, neither Brossart nor Dees demonstrated the ability of GP2-pulsed dendritic cells to prevent or delay recurrence of disease following remission. As with E75, cancer vaccines targeting "self" tumor antigens, like HER2/neu from which GP2 is derived, present unique challenges because of the immunologic tolerance characteristic of self proteins.

Peoples et al. have previously evaluated the use of GP2 for a peptide-based breast cancer vaccine trial by conducting in vitro cytotoxicity assays with GP2-pulsed dendritic cells and CD8 T cells obtained from breast cancer patients. (Mittendorf E A et al. Cancer (2006) 106:2309-2317.) While the results from these in vitro experiments confirmed the presence of GP2-specific precursor cytotoxic T lymphocytes in women with HER2/neu+ breast cancer, it was concluded that because of the variability of response to a given peptide and the heterogeneity of antigen expression in vivo, vaccination with multiple different peptides, including the immunodominant peptide E75, will be required to provide an adequate immune response. (Mittendorf E A et al. Cancer (2006) 106:2309-2317.)

As noted above, trastuzumab is indicated for HER2/neu over-expressing (IHC 3$^+$ or FISH≥2.0), node-positive (NP), metastatic breast cancer patients, and shows very limited activity in patients with low to intermediate HER2/neu expression. Similarly, in the studies discussed above, patients receiving the E75 and GP2-based vaccines were selected, in part, based on the presence of tumors that over-expressed HER2/neu. Accordingly, a GP2 peptide vaccine would not be expected to be effective in cancer patients with low and intermediate levels of HER2/neu tumor expression.

SUMMARY

In one embodiment, the invention features methods of preventing cancer recurrence in a subject who has HER2/neu expressing tumor cells. In a preferred embodiment, the method is directed to preventing breast cancer recurrence in a subject who is in remission following treatment with a standard course of therapy. In one embodiment, the standard course of therapy is treatment with trastuzumab, which treatment may continue concurrently with the methods described herein. The methods comprise administering to the subject an effective amount of a composition comprising a pharmaceutically effective carrier and a GP2 peptide. Preferably the GP2 peptide has the amino acid sequence of SEQ ID NO:2. In one embodiment, other than the GP2 peptide, the composition does not contain any other HER2/neu-derived peptides, including, for example, the immunodominant peptide E75. The administration can be accomplished by any means suitable in the art, such as inoculation or injection, and more particularly intradermal injection, which can occur with one or more separate doses. Such doses may comprise an equal concentration of the peptide and an immunoadjuvant, may be administered substantially concurrently, and can be administered at one inoculation site or spaced apart from each other on the surface of the skin. The composition can be administered approximately three to six times or more on a monthly basis until a protective immunity is established. In some aspects, the composition further comprises an adjuvant such as granulocyte macrophage-colony stimulating factor (GM-CSF) and preferably recombinant human GM-CSF.

In some aspects, the methods further comprise administering to the subject a booster vaccine dose, which comprises an effective amount of a composition comprising a pharmaceutically effective carrier and a peptide having the amino acid sequence of SEQ ID NO:2. In some aspects, the composition of the booster further comprises an adjuvant such as GM-CSF and preferably recombinant human GM-CSF. The administration of a booster can be accomplished by any means suitable in the art, such as inoculation or injection, and more particularly intradermal injection, which can occur with one or more separate doses. Such doses may comprise an equal concentration of the peptide and an immunoadjuvant, may be administered substantially concurrently, and can be administered at one inoculation site or spaced apart from each other on the surface of the skin. Typically the booster is administered after a primary immunization schedule has been completed, and preferably every six or 12 months after the primary immunization, as needed.

The subject can be any mammal, and is preferably a human. In certain aspects, the human is positive for major histocompatibility antigen blood-typed as human leukocyte antigen A2 or human leukocyte antigen A3. In other aspects, cancer cells from the human are positive for the expression of detectable levels of HER2/neu. In some aspects, the cancer cells exhibit low or intermediate expression of HER2/neu. For example, in some preferred aspects, the cancer cells from the human have an immunohistochemistry (IHC) rating of 1+ or 2+ and/or a fluorescence in situ hybridization (FISH) rating of less than 2.0). In other aspects, the cancer cells from the human may have an IHC rating up to 3+. In other aspects, the cancer cells from the human can exhibit over-expression of HER2/neu. For example, in some preferred aspects, the cancer cells from the human have an immunohistochemistry (IHC) rating of 3+ and/or a fluorescence in situ hybridization (FISH) rating of greater than or equal to 2.0). In other embodiments, the human does not have pre-existing immunity to GP2 (SEQ ID NO:2 or SEQ ID NO:4).

In another embodiment, the invention provides compositions for use in the methods described in this application. In one aspect, the compositions comprise a pharmaceutically acceptable carrier, an effective amount of a peptide having the amino acid sequence of SEQ ID NO:2, and an adjuvant, such as granulocyte macrophage-colony stimulating factor. The compositions are preferably administered in an optimized immunization schedule. In one embodiment, the vaccine composition comprises 0.1-1 mg/ml peptide and 0.125-0.5 mg/ml adjuvant. In some specific aspects, the preferred concentrations and schedules of the vaccine composition include: (1) 1 mg/ml peptide and 0.25 mg/ml adjuvant, (2) 0.5 mg/ml peptide and 0.25 mg/ml adjuvant, (3) 0.1 mg/ml peptide and 0.25 mg/ml adjuvant, (4) 1 mg/ml peptide and 0.125 mg/ml adjuvant, and (5) 0.5 mg/ml peptide and 0.125 mg/ml adjuvant, each with monthly inoculations for at least 6 consecutive months followed by periodic booster inoculations (preferably semi-annually or annually) for 1 year, 2 years, or 3 or more years.

BRIEF DESCRIPTION OF THE DRAWINGS

The accompanying drawings, which are included to provide a further understanding of the invention and are incorporated in and constitute a part of this specification, illustrate aspects of the invention and together with the description serve to explain the principles of the invention. In the drawings.

DETAILED DESCRIPTION

Figure 1A:
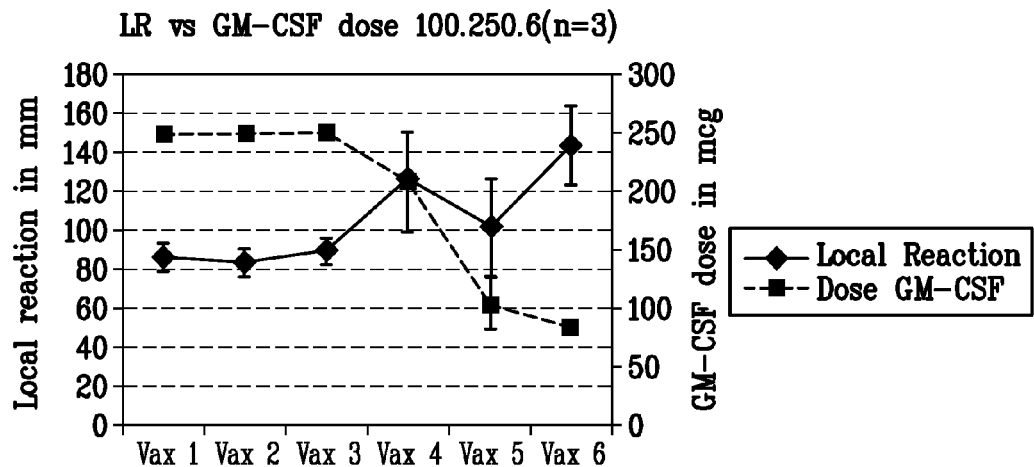
FIG. 1 shows the mean local reactions vs. GM-CSF dose by dose groups. Patients were vaccinated with peptide and GM-CSF in four dose groups. A. 100 mcg peptide/250 mcg GM-CSF dose group. B. 500 mcg peptide/250 mcg GM-CSF dose group. C. 1000 mcg peptide/250 mcg GM-CSF dose group. D. 500 mcg peptide/125 mcg GM-CSF dose group. Local reactions were measured in millimeters (solid lines). A local reaction ≥100 mm induration necessitated a 50% dose reduction in GM-CSF dose (dashed lines). There were no peptide dose reductions.
Figure 1B:
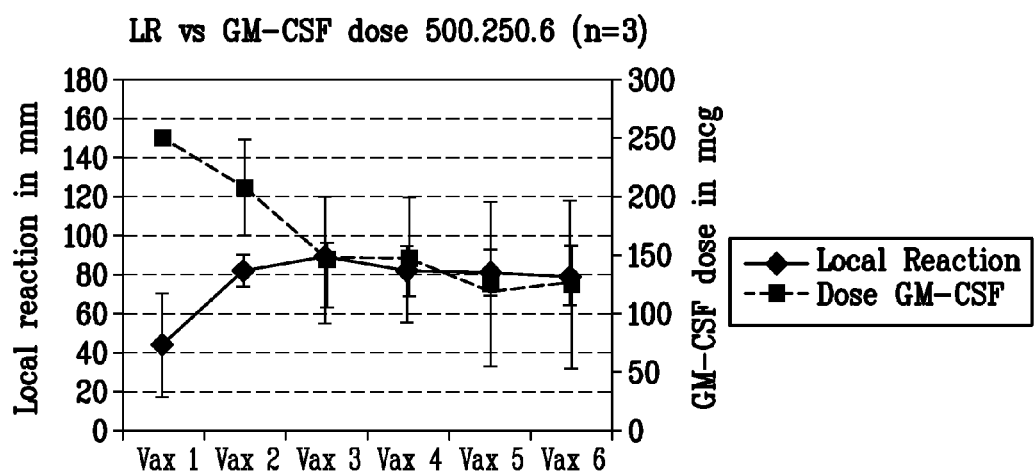
Figure 1C:
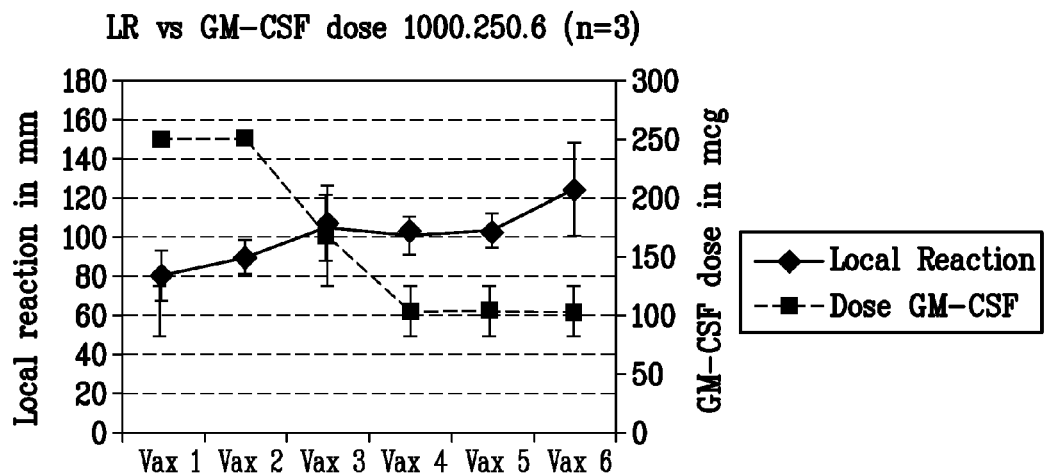
Figure 1D:
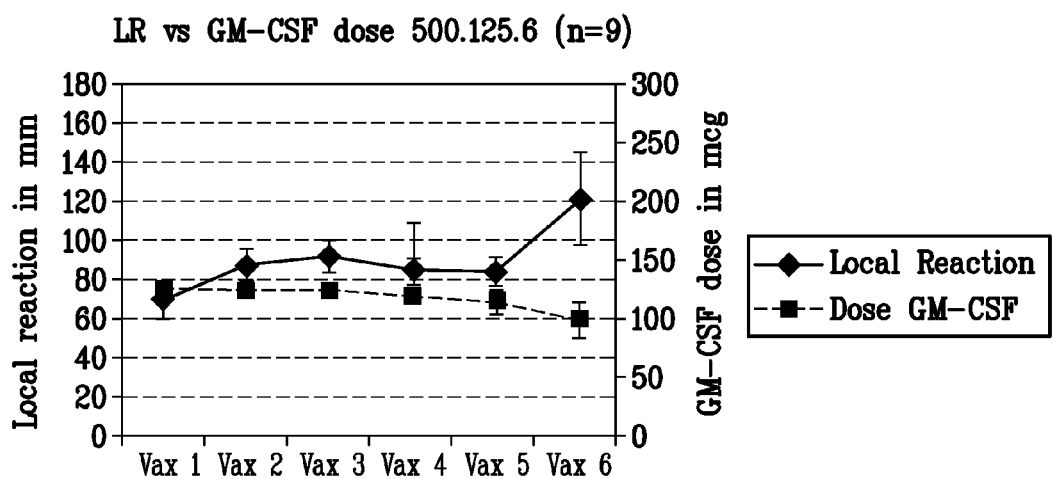

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The term "prevent" or "prevention" refers to any success or indicia of success in the forestalling or delay of breast cancer recurrence/relapse in patients in clinical remission, as measured by any objective or subjective parameter, including the results of a radiological or physical examination.

"Effective amount" or "therapeutically effective amount" are used interchangeably herein, and refer to an amount of a compound, material, or composition, as described herein effective to achieve a particular biological result such as, but not limited to, biological results disclosed, described, or exemplified herein. Such results may include, but are not limited to, the prevention of breast cancer, and more particularly, the prevention of recurrent breast cancer, e.g., the prevention of relapse in a subject, as determined by any means suitable in the art. Optimal therapeutic amount refers to the dose, schedule and the use of boosters to achieve the best therapeutic outcome.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

"Protective immunity" or "protective immune response," means that the subject mounts an active immune response to an immunogenic component of an antigen such as the breast cancer antigens described and exemplified herein, such that upon subsequent exposure to the antigen, the subject's immune system is able to target and destroy cells expressing the antigen, thereby decreasing the incidence of morbidity and mortality from recurrence of cancer in the subject. Protective immunity in the context of the present invention is preferably, but not exclusively, conferred by T lymphocytes.

"Pre-existing immunity" is defined as a peptide-specific dimer level of at least 0.3%. The peptide-specific dimer level can be measured using standard assays, such as the HLA-A2 immunoglobulin dimer assay described in this application.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Peptide" refers to any peptide comprising two or more amino acids joined to each other by peptide bonds or modified peptide bonds, i.e., peptide isosteres. Polypeptide refers to both short chains, commonly referred to as peptides, oligopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

"Booster" refers to a dose of an immunogen administered to a patient to enhance, prolong, or maintain protective immunity and to overcome the down-regulation of T-cell responses mediated by regulatory T-cells.

"Free of breast cancer" or "disease free" or NED (No Evidence of Disease) means that the patient is in clinical remission induced by treatment with the current standard of care therapies. By "remission" or "clinical remission," which are used synonymously, it is meant that the clinical signs, radiological signs, and symptoms of breast cancer have been significantly diminished or have disappeared entirely based on clinical diagnostics, although cancerous cells may still exist in the body. Thus, it is contemplated that remission encompasses partial and complete remission. The presence of residual cancer cells can be enumerated by assays such as CTC (Circulating Tumor Cells) and may be predictive of recurrence.

"Relapse" or "recurrence" or "resurgence" are used interchangeably herein, and refer to the radiographic diagnosis of return, or signs and symptoms of return of breast cancer after a period of improvement or remission.

Breast cancer is a major health concern for women worldwide. Breast cancer vaccines that have been attempted to date have been limited in efficacy, particularly with respect to preventing relapse in patients who are in remission following a standard course of therapy. As discussed in this application, it has been determined that administering a peptide of the HER2/neu oncogene, GP2 (SEQ ID NO:2), can induce a potent in vivo immune response that is known to correlate with a reduced rate of recurrence of breast cancer in disease-free patients.

The GP2 peptide is associated with MHC HLA-A2, and thus may induce protective immunity in patients having the HLA-A2 haplotype. The HLA-A2 haplotype has been implicated as a negative prognostic factor in ovarian (Gamzatova et al., Gynecol Oncol (2006) 103:145-50) and prostate cancer (Hueman et al., Clin Cancer Res (2005) 11:7470-79; De Petris et al., Med Oncol (2004) 21:49-52) and this finding likely extends to breast cancer as well. Thus, HLA-A2$^+$ patients seem to represent a higher risk to develop cancer recurrence following remission. Nevertheless, it was unexpectedly demonstrated that a vaccine composition comprising GP2+GM-CSF effectively induced a potent in vivo immune response in HLA-A2$^+$ patients that is known to correlate with a lower risk of breast cancer recurrence and longer disease-free survival as compared to HLA-A2$^-$ control patients. Moreover, it was surprisingly found that patients treated with GP2 (the subdominant epitope) and GM-CSF exhibited more robust DTH responses as compared to vaccine compositions comprising E75 (the immunodominant epitope) and GM-CSF. Notably, these results were not obtained by combining GP2 with another epitope, such as E75 to generate a multiepitope vaccine, but instead were obtained with a single epitope (i.e., GP2) vaccine. In addition, based on preliminary data, it appears that GP2 can also induce protective immunity in patients having the HLA-A3 haplotype.

Because GP2 is derived from the HER2/neu protein, one would expect that patients overexpressing HER2/neu would exhibit a better response to a GP2-based vaccine than those with low to intermediate HER2/neu expression. For example, another HER2/neu based therapy, trastuzumab (Herceptin® Genentech Inc., South San Francisco, Calif.), is only indicated for HER2/neu over-expressing (IHC 3$^+$ or FISH≥2.0), node-positive (NP), metastatic breast cancer patients, and shows very limited activity in patients with low to intermediate HER2/neu expression. Nevertheless, it was unexpectedly observed that patients having low to intermediate levels of HER2/neu expression experienced potent immune responses to GP2, similar in magnitude to GP2-induced responses in patients overexpressing HER2/neu.

Accordingly, one embodiment of the present invention features vaccine compositions for inducing protective immunity against breast cancer relapse or recurrence. Another embodiment provides methods for inducing and for maintaining protective immunity against breast cancer, and more particularly against recurrent breast cancer. In some aspects, the methods comprise administering to a subject an effective amount of a composition comprising a pharmaceutically effective carrier, a polypeptide having the amino acid sequence of SEQ ID NO:2, and optionally an immunoadjuvant, such as GM-CSF. Variants of SEQ ID NO:2, including those with modified side chains of amino acids as described by U.S. Pat. Publ. No. 20050169934, which is hereby incorporated by reference in its entirety, are suitable for use in the vaccine compositions and methods of this application.

In addition, a naturally occurring polymorphism at codon 655 (isoleucine to valine substitution) has been identified, yielding a polymorphic GP2 peptide having the sequence IVSAVVGIL (SEQ ID NO:4) (Papewalis et al., Nucleic Acid Res. (1991) 19:5452). This polymorphic GP2 peptide is also suitable for use in the vaccine compositions and methods of this application. Similarly, several groups have investigated single, double, and triple amino-acid substitutions introduced at various sites in the GP2 peptide, including the anchor residues (positions 2 and 9), and found that certain amino acid substitutions lead to increased binding of GP2 to HLA-A2 (Tanaka et al., Int J Cancer (2001) 94:540-44; Kuhns et al., J Biol Chem (1999) 274:36422-427; Sharma et al., J Biol Chem (2001) 276:21443-449, each of these references is hereby incorporated by reference in its entirety). Thus, one of skill in the art would understand that certain substitutions, particularly at the anchor residues, could be made to GP2 without negatively affecting its ability to induce a protective immune response. In one embodiment, the GP2 peptide comprises the amino acid sequence of SEQ ID NO:2 or SEQ ID NO:4 except for a substitution at a residue that increases the affinity of the GP2 peptide for the HLA-A2 molecule. Preferably, the substitution occurs at one or both of the anchor residues of GP2 (positions 2 and 9). More preferably, the substitution comprises an isoleucine to leucine substitution at position 2 and/or a leucine to valine substitution at position nine. In another embodiment, the GP2 peptide comprises the amino acid sequence of SEQ ID NO:2 or SEQ ID NO:4 except for a substitution at a residue that does not affect the affinity of the GP2 peptide for the HLA-A2 molecule as compared to the affinity of a wild type GP2 peptide comprising SEQ ID NO:2 for the HLA-A2 molecule. Assays to test for binding affinity between GP2 and HLA-A2 are well-known in the art and include, for example, the T2 cell surface assembly assay disclosed in Sharma et al., J Biol Chem (2001) 276:21443-449.

In one aspect, the GP2 peptide has no more than 9, 10, 11, 12, 13, 14, or 15 amino acid residues. In one embodiment, the GP2 peptide has no more than 9 amino acid residues. Preferably, the GP2 peptide with no more than 9 amino acids is SEQ ID NO:2 or SEQ ID NO:4, or a mutant version of SEQ ID NO:2 or SEQ ID NO:4 with a substitution at position 2 and/or 9.

The subject can be any animal, and preferably is a mammal such as a human, mouse, rat, hamster, guinea pig, rabbit, cat, dog, monkey, cow, horse, pig, and the like. Humans are most preferred. In highly preferred aspects, the humans are positive for the HLA-A2 haplotype. In other preferred aspects, the humans are positive for the expression of human HER2/neu, including preferentially humans with low and/or intermediate HER2/neu expressing tumors, as well as humans that are overexpressors of HER2/neu.

Additionally, our group has previously demonstrated a possible synergy between trastuzumab and GP2-peptide stimulated CTLs ex vivo. Pre-treatment of breast cancer cells with trastuzumab followed by incubation with GP2-peptide induced CTLs resulted in enhanced cytotoxicity in three tumor cell lines compared to treatment with trastuzumab or GP2-specific CTLs alone (Mittendorf E A et al., Annals of Surgical Oncology (2006) 13(8):1085-1098). In view of the results from the experiments with GP2 disclosed in this application, these findings indicate that concurrent GP2 vaccination during trastuzumab therapy may be an effective combination immunotherapy.

The vaccine compositions can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form.

The vaccine compositions can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine compositions are preferably formulated for inoculation or injection into the subject. For injection, the vaccine compositions of the invention can be formulated in aqueous solutions such as water or alcohol, or in physiologically compatible buffers such as Hanks's solution, Ringer's solution, or physiological saline buffer. The solution may contain formulatory agents such as suspending, preserving, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The vaccine compositions can also be formulated in sustained release vehicles or depot preparations. Such long acting formulations may be administered by inoculation or implantation (for example subcutaneously or intramuscularly) or by injection. Thus, for example, the vaccine compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers.

The vaccine compositions can comprise agents that enhance the protective efficacy of the vaccine, such as adjuvants. Adjuvants include any compound or compounds that act to increase a protective immune response to the GP2 peptide antigen, thereby reducing the quantity of antigen necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (*M. phlei*) cell wall extract (MCWE) (U.S. Pat. No. 4,744,984), *M. phlei* DNA (M-DNA), and M-DNA-*M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof. GM-CSF is highly preferred.

Vaccine compositions comprising GP2 peptide antigens and further comprising adjuvants can be prepared using techniques well known to those skilled in the art including, but not limited to, mixing, sonication and microfluidation. The adjuvant can comprise from about 10% to about 50% (v/v) of the vaccine composition, more preferably about 20% to about 40% (v/v), and more preferably about 20% to about 30% (v/v), or any integer within these ranges. About 25% (v/v) is highly preferred.

Administration of the vaccine compositions can be by infusion or injection (e.g., intravenously, intramuscularly, intracutaneously, subcutaneously, intrathecal, intraduodenally, intraperitoneally, and the like). The vaccine compositions can also be administered intranasally, vaginally, rectally, orally, or transdermally. Additionally, vaccine compositions can be administered by "needle-free" delivery systems. Preferably, the compositions are administered by intradermal injection. Administration can be at the direction of a physician or physician assistant.

The injections can be split into multiple injections, with such split inoculations administered preferably substantially concurrently. When administered as a split inoculation, the dose of the immunogen is preferably, but not necessarily, proportioned equally in each separate injection. If an adjuvant is present in the vaccine composition, the dose of the adjuvant is preferably, but not necessarily, proportioned equally in each separate injection. The separate injections for the split inoculation are preferably administered substantially proximal to each other on the patient's body. In some preferred aspects, the injections are administered at least about 1 cm apart from each other on the body. In some preferred aspects, the injections are administered at least about 2.5 cm apart from each other on the body. In highly preferred aspects, the injections are administered at least about 5 cm apart from each other on the body. In some aspects, the injections are administered at least about 10 cm apart from each other on the body. In some aspects, the injections are administered more than 10 cm apart from each other on the body, for example, at least about 12.5, 15, 17.5, 20, or more cm apart from each other on the body. Primary immunization injections and booster injections can be administered as a split inoculation as described and exemplified herein.

Various alternative pharmaceutical delivery systems may be employed. Non-limiting examples of such systems include liposomes and emulsions. Certain organic solvents such as dimethylsulfoxide also may be employed. Additionally, the vaccine compositions may be delivered using a sustained-release system, such as semipermeable matrices of solid polymers containing the therapeutic agent. The various sustained-release materials available are well known by those skilled in the art. Sustained-release capsules may, depending on their chemical nature, release the vaccine compositions over a range of several days to several weeks to several months.

To prevent breast cancer recurrence in a patient who is in breast cancer remission, a therapeutically effective amount of the vaccine composition is administered to the subject. A therapeutically effective amount will provide a clinically significant increase in the number of GP2-specific cytotoxic T-lymphocytes (CD8$^+$) in the patient, as well as a clinically significant increase in the cytotoxic T-lymphocyte response to the antigen, as measured by any means suitable in the art. In addition, due to epitope spreading, a therapeutically effective amount of the GP2 vaccine composition will provide an increase in the number of E75-specific cytotoxic T-lymphocytes (CD8$^+$) in the patient, as measured by any means suitable in the art. In the patient on the whole, a therapeutically effective amount of the vaccine composition will destroy residual microscopic disease and significantly reduce or eliminate the risk of recurrence of breast cancer in the patient.

The effective amount of the vaccine composition may be dependent on any number of variables, including without limitation, the species, breed, size, height, weight, age, overall health of the patient, the type of formulation, the mode or manner or administration, or the presence or absence of risk factors that significantly increase the likelihood that the breast cancer will recur in the patient. Such risk factors include, but are not limited to the type of surgery, status of lymph nodes and the number positive, the size of the tumor, the histologic grade of the tumor, the presence/absence of hormone receptors (estrogen and progesterone receptors), HER2/neu expression, lymphovascular invasion, and genetic predisposition (BRCA 1 and 2). In some preferred aspects, the effective amount is dependent on whether the patient is lymph node positive of lymph node negative, and if the patient is lymph node positive, the number and extent of the positive nodes. In all cases, the appropriate effective amount can be routinely determined by those of skill in the art using routine optimization techniques and the skilled and informed judgment of the practitioner and other factors evident to those skilled in the art. Preferably, a therapeutically effective dose of the vaccine compositions described herein will provide the therapeutic preventive benefit without causing substantial toxicity to the subject.

Toxicity and therapeutic efficacy of the vaccine compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Vaccine compositions that exhibit large therapeutic indices are preferred. Data obtained from cell culture assays and animal studies can be used in formulating a range of dosage for use in patients. The dosage of such vaccine compositions lies preferably within a range of circulating concentrations that include the ED50 with little or no toxicity. The dosage may vary within this range depending upon the dosage form employed and the route of administration utilized.

Toxicity information can be used to more accurately determine useful doses in a specified subject such as a human. The treating physician can terminate, interrupt, or adjust administration due to toxicity, or to organ dysfunctions, and can adjust treatment as necessary if the clinical response is not adequate, to improve the response. The magnitude of an administrated dose in the prevention of recurrent breast cancer will vary with the severity of the patient's condition, relative risk for recurrence, or the route of administration, among other factors. The severity of the patient's condition may, for example, be evaluated, in part, by standard prognostic evaluation methods.

The vaccine compositions can be administered to a patient on any schedule appropriate to induce and/or sustain protective immunity against breast cancer relapse, and more specifically to induce and/or sustain a cytotoxic T lymphocyte response to GP2 and/or E75 (due to epitope spreading). For example, patients can be administered a vaccine composition as a primary immunization as described and exemplified herein, followed by administration of a booster to bolster and/or maintain the protective immunity.

In some aspects, patients can be administered the vaccine compositions 1, 2 or more times per month. Once per month for six consecutive months is preferred to establish the protective immune response, particularly with respect to the primary immunization schedule. In some aspects, boosters can be administered at regular intervals such as every 6 or more months after completion of the primary immunization schedule. Administration of the booster is preferably every 6 months. Boosters can also be administered on an as-needed basis.

The vaccine administration schedule, including primary immunization and booster administration, can continue as long as needed for the patient, for example, over the course of several years, to over the lifetime of the patient. In some aspects, the vaccine schedule includes more frequent administration at the beginning of the vaccine regimen, and includes less frequent administration (e.g., boosters) over time to maintain the protective immunity.

The vaccine can be administered at lower doses at the beginning of the vaccine regimen, with higher doses administered over time. The vaccines can also be administered at higher doses at the beginning of the vaccine regimen, with lower doses administered over time. The frequency of primary vaccine and booster administration and dose of GP2 administered can be tailored and/or adjusted to meet the particular needs of individual patients, as determined by the administering physician according to any means suitable in the art.

In some aspects, the vaccine compositions, including compositions for administration as a booster, comprise from about 0.1 mg to about 10 mg of GP2 peptide. In some preferred aspects, the compositions comprise about 0.1 mg of GP2. In some preferred aspects, the compositions comprise about 1 mg of GP2. In some most preferred aspects, the compositions comprise about 0.5 mg of GP2.

In some preferred aspects, the vaccine compositions comprising GP2, including compositions for administration as a booster, further comprise GM-CSF. Such compositions preferably comprise from about 0.01 mg to about 0.5 mg of GM-CSF. In some preferred aspects, the compositions comprise about 0.125 mg of GM-CSF. In some preferred aspects, the compositions comprise about 0.25 mg of GM-CSF.

In some particularly preferred aspects, the vaccine compositions comprise about 0.5 mg to 1 mg of GP2 peptide and from 0.125 to 0.250 mg of GM-CSF in a total volume of 1 ml, and are administered monthly as a split inoculation of 0.5 ml each, administered by injections about 5 cm apart on the patient's body, and administered concurrently or admixed. The administration schedule is preferably monthly for six months. After a period of about 48 hours, the injection site can be assessed for local reaction of erythema and induration. If the reactions at both sites are confluent and the area of total induration measures >100 mm (or the patient experiences any >grade 2 systemic toxicity), then the dose of GM-CSF may be reduced, for example, by half, though it is intended that the peptide dose remain the same. If the patient presents a robust reaction on subsequent doses, then further reduction of GM-CSF can occur, for example, reducing by half. If the patient does not present with a robust reaction, then the patient can continue with the higher GM-CSF dose. In some aspects, the administration schedule and dosing of the booster is similarly determined, with boosters beginning with administration of vaccine compositions comprising 1 mg of GP2 and 0.25 mg GM-CSF, administered about every six months following the conclusion of the primary immunization vaccine schedule.

The following examples are provided to describe the invention in greater detail. They are intended to illustrate, not to limit, the invention.

Example 1

Phase I Trial of GP2+GM-CSF

Patient Characteristics and Clinical Protocol:

This is the first phase I clinical trial of the HER2/neu-derived GP2-peptide with the GM-CSF immunoadjuvant in disease-free breast cancer patients. The trial was Institutional Review Board-approved and conducted at Walter Reed Army Medical Center under an investigational new drug application (BB-IND #11730). All patients had histologically confirmed node-negative breast cancer that expressed all levels of HER2/neu by standard immunohistochemistry (IHC 1-3+). Patients had completed a standard course of surgery, chemotherapy, and radiation therapy (as required) prior to enrollment, and those patients on hormonal chemoprevention were continued on their specific regimen. After screening for eligibility criteria and proper counseling and consenting, eligible HLA-A2+ patients were enrolled into the study. Before vaccination, patients were skin tested with a panel of recall antigens (Mantoux test). Patients were considered immunocompetent if they reacted (>5 mm) to ≥2 antigens.

We enrolled and vaccinated 18 node-negative, disease-free breast cancer patients with all levels of HER2/neu expression (IHC 1-3+). No patients withdrew from this study or were lost to follow up. Patient demographics, prognostic factors, and treatment profiles are presented in Table 1.

TABLE 1

Patient demographics, prognostic factors, and treatment profiles for Phase I Study.

|  | GP2 Patients (n = 18) |
|---|---|
| Median age, years | 47 |
| Range, years | 32-68 |
| Race |  |
| White, # (%) | 14 (77.8) |
| Black, # (%) | 2 (11.1) |
| Other, # (%) | 2 (11.1) |
| Tumor size |  |
| T2-T4, # (%) | 7 (38.9) |
| Histological grade |  |
| Grade III, # (%) | 7 (38.9) |
| HER2/neu IHC 3$^+$ or FISH$^+$, # (%) | 6 (33.3) |
| Hormone receptor negative, # (%) | 8 (44.4) |

TABLE 1-continued

Patient demographics, prognostic factors, and treatment profiles for Phase I Study.

|  | GP2 Patients (n = 18) |
| --- | --- |
| No chemotherapy, # (%) | 6 (33.3) |
| No XRT, # (%) | 6 (33.3) |
| Hormonal therapy, # (%) | 9 (50.0) |

Vaccination And Clinical Protocol

Vaccine. The GP2-peptide (HER2/neu, 654-662) was commercially produced in accordance with federal guidelines for good manufacturing practices (GMP) by NeoMPS Inc. (San Diego, Calif.). Peptide purity (>95%) was verified by high-performance liquid chromatography and mass spectrometry, and the amino acid content was determined by amino acid analysis. Sterility, endotoxin (limulus amebocyte lysate test), and general safety testing was carried out by the manufacturer. Lyophilized peptide was reconstituted in sterile saline at the following concentrations: 100 mcg/0.5 ml, 500 mcg/0.5 ml, and 1 mg/0.5 ml. The GP2-peptide was mixed with GM-CSF (Berlex, Seattle, Wash.) at 250 mcg/0.5 ml, and the 1.0 ml inoculation was split and given intradermally at two sites 5 cm apart in the same extremity.

Vaccination Series.

The study was designed and conducted as a dose escalation safety trial to determine the safety, immunogenicity, and optimal best dose of the GP2-peptide in combination with the adjuvant GM-CSF. The optimal best dose was defined as the minimum dose of the vaccine and adjuvant that gives the best in vivo and ex vivo immunologic response.

Three patients were assigned to each of the first three dose groups receiving six monthly inoculations of GP2 and 250 mcg of GM-CSF. Dose groups are listed as GP2-peptide (mcg):GM-CSF(mcg):# of inoculations, and include: 100: 250:6, 500:250:6, and 1000:250:6. GM-CSF was reduced by 50% if patients developed a local reaction measuring >100 mm or >grade 2 systemic toxicities. In the last group of patients, GM-CSF was reduced to 125 mcg so that these nine patients received 500:125:6.

This dose escalation trial utilized an increasing GP2-peptide dose (100 mcg, 500 mcg, and 1000 mcg) with 250 mcg of GM-CSF and 6 monthly inoculations for the first three dose groups (abbreviated: GP2-peptide(mcg):GM-CSF(mcg):# inoculations—100:250:6, 500:250:6, and 1000:250:6). The GM-CSF was reduced by 50% if patients developed a local reaction measuring >100 mm or >grade 2 systemic toxicities. Eight of the first 9 patients (89%) required GM-CSF dose reductions due to robust local reactions. Due to the number of dose reductions required, the starting dose of GM-CSF was reduced from 250 mcg to 125 mcg per inoculation for the fourth and final group of 9 patients (500:125:6). Only 2 of the 9 patients (22%) in the final dose group required a further GM-CSF dose reduction. No peptide dose reductions were required for the vaccination series. FIG. 1 depicts the mean local reactions vs. the mean GM-CSF dose for each dose group. Local reactions in the final dose group fluctuated less throughout the vaccination series using a GM-CSF starting dose of 125 mcg per inoculation.

Toxicity.

Patients were observed one hour post-vaccination for immediate hypersensitivity and returned 48-72 hours later to have their injection sites measured and questioned about toxicities. Toxicities were graded by the NCI Common Terminology Criteria for Adverse Events, v3.0 (CTCAE). Progression from one dose group to the next occurred only in the absence of dose limiting toxicities, defined as hypersensitivity reaction or two patients within a dose group developing ≥grade 3 toxicity.

Peripheral Blood Mononuclear Cell (PBMC) Isolation and Cultures.

Blood was drawn before each vaccination and at one (post-vaccine) and six months (long-term) after vaccine series completion. 50 ml of blood was drawn and PBMCs were isolated. PBMCs were washed and re-suspended in culture medium and used as a source of lymphocytes.

HLA A2 Immunoglobulin Dimer Assay.

The presence of GP2-specific CD8+ T cells in freshly isolated PBMCs from patients was assessed directly ex vivo by the dimer assay at baseline, prior to each successive vaccination, and at 1, 6, and 12 months following completion of the vaccination series (Woll M M et al., J Clin Immunol (2004) 24:449-461). Briefly, the HLA-A2:Immunoglobulin (Ig) dimer (PharMingen, San Diego, Calif.) was loaded with the GP2, E75, or control peptide (E37, folate binding protein (25-33) RIAWARTEL) by incubating 1 mcg of dimer with an excess (5 mcg) of peptide and 0.5 mcg of β2-microglobulin (Sigma, St. Louis, Mo.) at 37° C. overnight then stored at 4° C. until used. PBMCs were washed and re-suspended in PharMingen Stain Buffer (PharMingen) and added at 5×10$^5$ cells/100 µl/tube in 5 ml round-bottom polystyrene tubes (Becton Dickinson, Mountain View, Calif.) and stained with the loaded dimers and antibodies. In each patient the level of GP2-specific and E75-specific CD8+ cells was determined in response to each successive vaccination, and average post-inoculation levels compared to pre-inoculation levels.

Delayed Type Hypersensitivity (DTH).

DTH reactions to the GP2-peptide were performed prior to, and following, the vaccination series. Intradermal injections, on the back or extremity (opposite side from vaccination), using 100 mcg of GP2 (without GM-CSF) in 0.5 mL saline were compared to an equal volume control inoculum of saline. DTH reactions were measured in two dimensions at 48-72 hours using the sensitive ballpoint pen method and reported as the orthogonal mean. Sokol J E, Measurement of delayed skin test responses. N Engl J Med (1975) 293:501-501.

Statistical Analysis.

P values for clinicopathological factors were calculated using Wilcoxon, Fisher's exact test or $\chi^2$ as appropriate. P values for comparing pre and post-vaccination DTH and dimer assays were calculated using Student t-test, paired or unpaired, as appropriate. Differences were considered significant when p<0.05.

Results

Compositions comprising GP2 and GM-CSF are both safe and highly immunogenic. The immune responses, both ex vivo and in vivo, appear to be influenced by the presence or absence of GP2-specific immunity at the initiation of the inoculation series and by the GM-CSF dose utilized. In addition, GP2 vaccination efficiently results in intra-antigenic epitope spreading.

Toxicity was limited to mild local reactions (which are desired and serve as a surrogate measure of immunogenicity) and mild systemic responses, many of which are known side effects of GM-CSF. There were no dose limiting toxicities, and dose reductions in GM-CSF were sufficient to limit the local reactions encountered with serial inoculations to grade 2. Overall the vaccine combination was well tolerated.

As discussed in further detail below, the ex vivo immunogenicity of the vaccine was demonstrated, but primarily evident when performing subgroup analysis of the patients without pre-existing immunity. Patients without pre-existing immunity, as previously defined as peptide specific dimer level <0.3%, achieved the greatest induction of a CTL response to GP2 vaccination. This response was uniform without regard to the dose of GP2-peptide. Patients with pre-existing immunity demonstrated a lesser CTL response which suggests either a level of tolerance to the peptide vaccinations, or a previously optimized endogenous immune response.

The in vivo immunogenicity of the GP2+GM-CSF vaccine was demonstrated by an increase in the DTH reaction in response to the GP2-peptide (without GM-CSF) before and after the vaccination series. This difference in response reached statistical significance cumulatively and within each dose group. Of note, patients without pre-existing immunity trended toward larger DTH reactions. Also, patients receiving the 250 mcg GM-CSF dose trended toward a larger DTH response, but this finding was confounded by a larger percentage of patients with pre-existing immunity in the lower GM-CSF dose group. Therefore, it is unclear if the difference seen in the 250 mcg GM-CSF patients is due to the adjuvant dose or lack of tolerance. Together, these DTH responses would indicate that in vivo immunity is maintained and augmented in all groups in response to vaccination.

Dose Groups.

This dose escalation trial utilized an increasing GP2-peptide dose (100 mcg, 500 mcg, and 1000 mcg) with 250 mcg of GM-CSF and 6 monthly inoculations for the first three dose groups (abbreviated: GP2-peptide(mcg):GM-CSF(mcg):# inoculations—100:250:6, 500:250:6, and 1000:250:6). The GM-CSF was reduced by 50% if patients developed a local reaction measuring ≥100 mm or ≥grade 2 systemic toxicities. Eight of the first 9 patients (89%) required GM-CSF dose reductions due to robust local reactions. Due to the number of dose reductions required, the starting dose of GM-CSF was reduced from 250 mcg to 125 mcg per inoculation for the fourth and final group of 9 patients (500:125:6). Only 2 of the 9 patients (22%) in the final dose group required a further GM-CSF dose reduction. No peptide dose reductions were required for the vaccination series. FIG. 1 depicts the mean local reactions vs. the mean GM-CSF dose for each dose group. Local reactions in the final dose group fluctuated less throughout the vaccination series using a GM-CSF starting dose of 125 mcg per inoculation.

Combined Dosing Group.

Figure 2A:
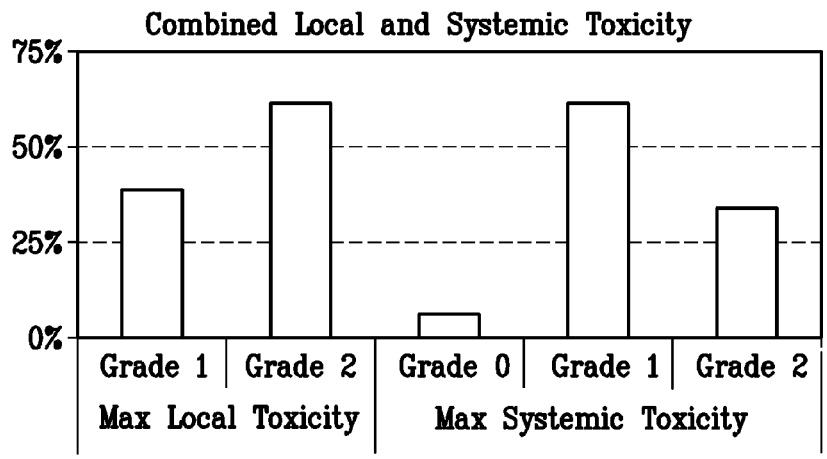
FIG. 2 shows toxicity and immunologic responses of all patients enrolled in GP2 phase I trial. A. Toxicity—no patients experience grade 3-5 local or systemic toxicities. B. Ex vivo immune response—pre-max % specific $CD8^+$ T-cells statistically increased (p=0.001). C. In vivo immune response—GP2 pre-post DTH statistically increased (p=0.0002). Normal saline (NS) control also shown for comparison.

There were no grade 3-5 toxicities among the 18 patients receiving a total of 108 doses of GP2+GM-CSF. Among all patients, maximum local toxicities occurring during the entire series were grade 1 (38.9%) or grade 2 (61.1%). Maximum systemic toxicities during the series were grade 0 (5.6%), grade 1 (61.1%), and grade 2 (33.3%). The most common local reactions included erythema and induration (100% of patients), pruritis (25%), and inflammation (23%). The most common systemic reactions were grade 1 fatigue (40%) and grade 1 arthralgia/myalgia (15%). Overall combined local and systemic toxicity rates are noted in FIG. 2a.

Figure 2B:
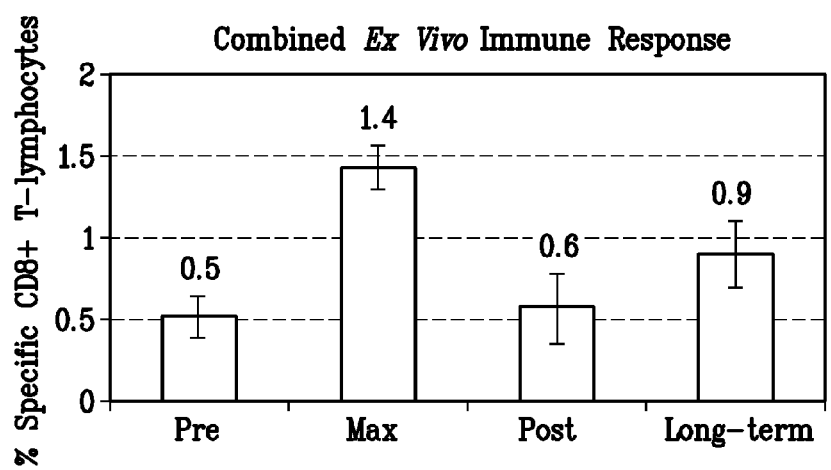

The GP2+GM-CSF vaccine was capable of eliciting an immune response both ex vivo and in vivo. Ex vivo immune response was assessed via HLA-A2:Ig dimer assay to detect the percentage of circulating GP2-specific $CD8^+$ T cells. GP2-specific CTLs are reported as the mean± standard error percentage of the total circulating $CD8^+$ population. Time points analyzed include pre-vaccine (pre=0.5±0.1%), one month after completion of all inoculations (post=0.6±0.1%), maximum value during series (max=1.4±0.2%), and 6 months after completion of all inoculations (long-term=0.9±0.2%). While a statistically significant increase occurred in patients when comparing pre vs. maximum vaccine level (p=0.0003), no significant increase was seen comparing pre vs. post or long-term vaccine dimer levels (p=0.7 and p=0.2, respectively) (FIG. 2b).

Figure 2C:
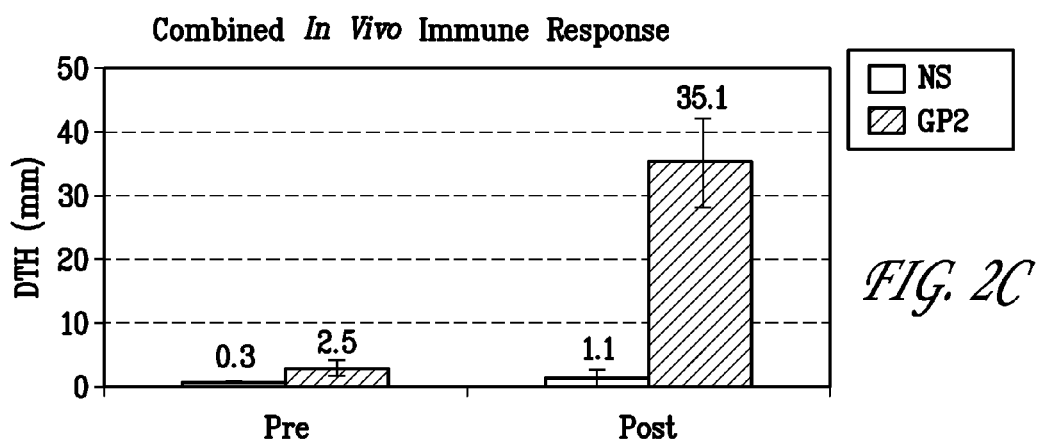

The vaccine's in vivo effectiveness was analyzed via pre and post-vaccine series DTH responses using GP2 (without GM-CSF) as well as a saline volume control. A statistically significant increase was noted in GP2 pre vs. post-vaccine DTH responses (2.5±1.4 mm vs. 35.1±7.0 mm, p=0.0002) (FIG. 2c).

To better elucidate the immunologic response to the GP2 vaccine, two different sub-set analyses were performed: response based on the presence of pre-existing GP2-specific immunity and response based on dose of GM-CSF. These are provided below.

Pre-Existing Vs. No Pre-Existing Immunity.

As previously defined, pre-existing immunity is a peptide specific dimer level >0.3% (Peoples G E et al., *J Clin Oncol* (2005) 23:7536-7545). Ten patients (56%) had dimer levels consistent with pre-existing immunity to GP2, and 8 patients (44%) had no pre-existing immunity. There was a statistical difference between the two groups pre-vaccine GP2-dimer levels (0.8+0.1% vs. 0.06+0.02%, p=0.0007).

Figure 3A:
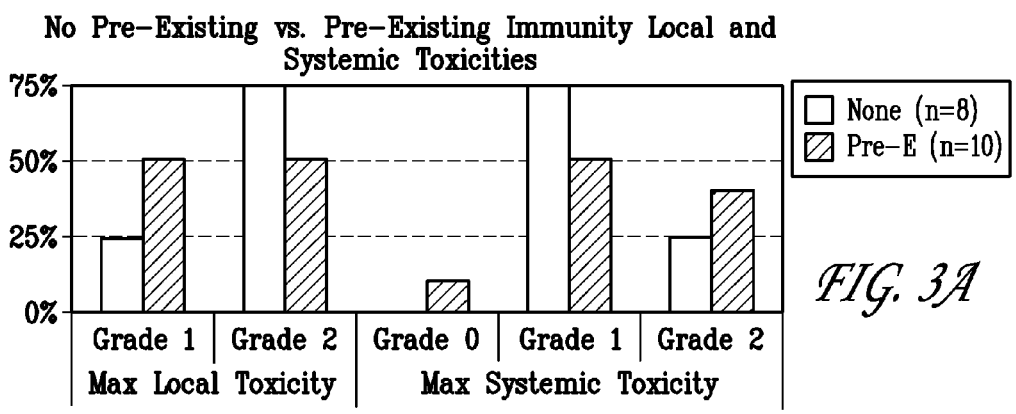
FIG. 3 shows toxicity and immunologic responses of patients enrolled in GP2 phase I trial comparing no pre-existing immunity (pre-dimer<0.03) vs. pre-existing immunity (pre dimer>0.03). A. Toxicity—toxicities were slightly increased in the no pre-existing immunity patients, albeit not significantly. B. Ex vivo immune response—Patients without pre-existing immunity showed statistically significant increases in pre-max, pre-post, and pre-long term % specific $CD8^+$ T-cells (p=0.003, p=0.03, and p=0.01 respectively) in response to vaccination. C. In vivo immune response—both pre-post DTH responses statistically increased (None p=0.03 and Pre-E p=0.0004). No statistical difference between post DTH responses was noted (p=0.3).

Patients without pre-existing immunity had slightly increased local reactions with slightly higher local toxicities compared to the group with pre-existing immunity; although, this was not statistically significant (FIG. 3a).

Figure 3B:
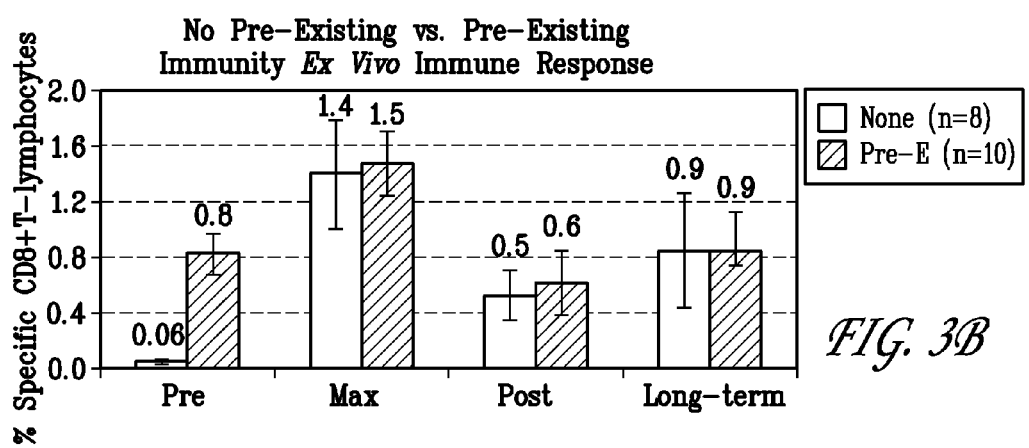

Ex vivo and in vivo immune responses were observed in both groups, but were more robust in the group of patients without pre-existing immunity. GP2 dimer levels from the group without pre-existing immunity were pre vs. max (0.06±0.02% vs. 1.4±0.4%; p=0.009), pre vs. post (0.06±0.02% vs. 0.5±0.2%; p=0.07), and pre vs. long-term (0.06+0.02% vs. 0.9+0.4%; p=0.06). In the 10 patients with pre-existing immunity, the CTL response to vaccination was pre vs. max (0.8±0.1% vs. 1.5±0.2%; p=0.02), pre vs. post (0.8±0.1% vs. 0.6±0.2%; p=0.2), and pre vs. long-term (0.8±0.1 vs. 0.9±0.2; p=0.7) (FIG. 3b).

When comparing the groups in vivo immune responses both groups had statistically significant increases in their pre vs. post DTH responses (no pre-existing immunity=3.3±2.1 mm vs. 43.9±14.6 mm; p=0.02; and pre-existing immunity=2.0±2.0 mm vs. 28.0±4.6 mm; p=0.0001).

Figure 3C:
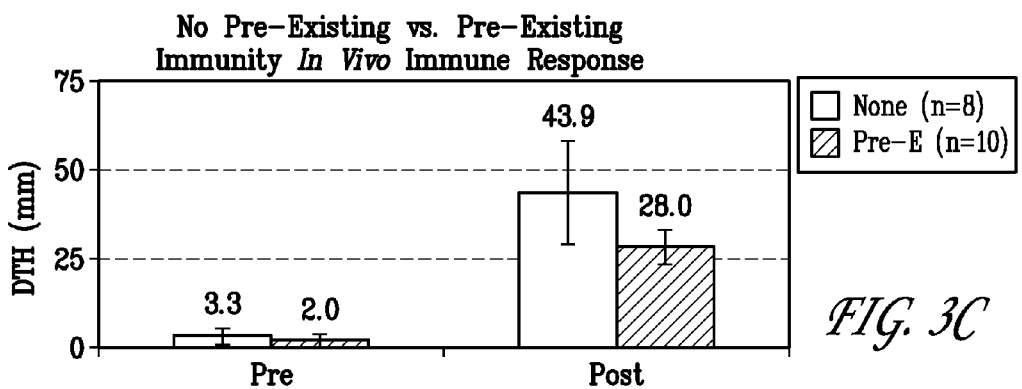

Patients without pre-existing immunity had larger post DTH responses compared to the post DTH response of the group with pre-existing immunity, but this difference was not statistically significant (43.9+14.6 mm vs. 28.0+4.6 mm, respectively; p=0.3) (FIG. 3c).

GM-CSF 250 mcg vs. 125 mcg.

Figure 4A:
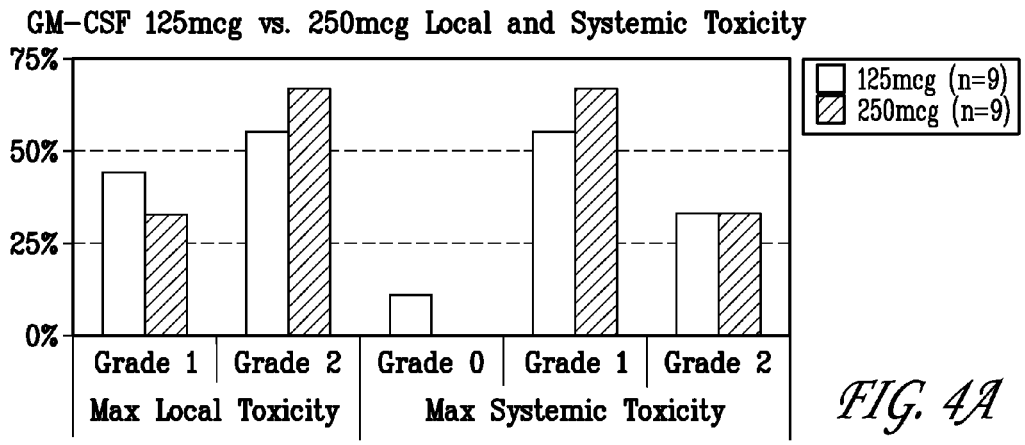
FIG. 4 shows toxicity and immunologic responses of patients enrolled in GP2 phase I trial comparing GM-CSF dose 125 mcg vs. 250 mcg. A. Toxicity—toxicities were slightly increased in the GM-CSF 250 mcg patients, albeit not significantly. B. Ex vivo immune response—the GM-CSF 125 mcg pre-max % specific $CD8^+$ T-cells did not statistically increase (p=0.17), but the GM-CSF 250 mcg pre-max % specific $CD8^+$ T-cells did statistically increase (p=0.005). C. In vivo immune response—GM-CSF 125 mcg and 250 mcg pre-post DTH statistically increased (respectively, p=0.009 and p=0.008). There was no statistical significance between GM-CSF 125 mcg post DTH and GM-CSF 250 mcg post DTH (p=0.1).

Analysis of the patients according to the two starting doses of GM-CSF was also performed. Both local and systemic toxicities were decreased in the final dose group of 125 mcg GM-CSF, albeit not statistically significant (FIG. 4a).

Figure 4B:
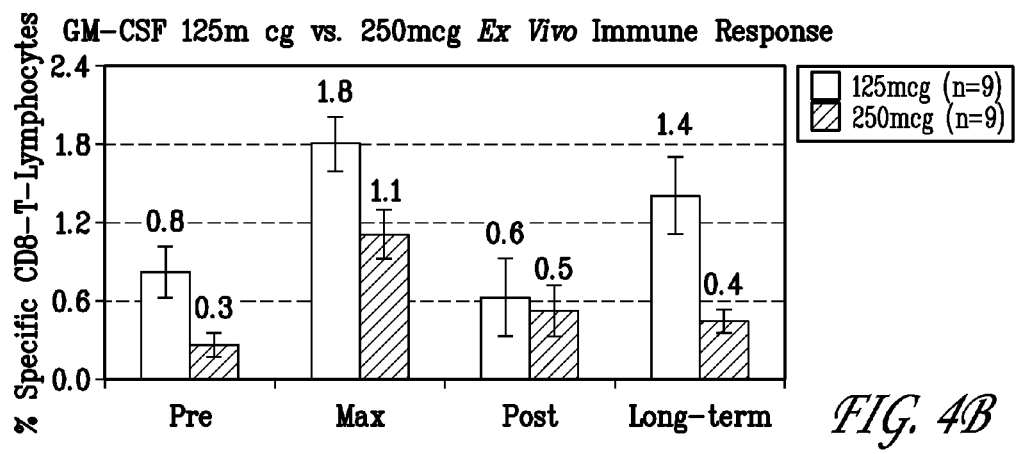

CTL response to vaccination in the 250 mcg dose groups (n=9) were pre vs. max (0.3±0.1% vs. 1.1±0.2%; p=0.004), pre vs. post (0.3±0.1% vs. 0.5±0.2%; p=0.07), and pre vs. long-term (0.3±0.1% vs. 0.4±0.09%; p=0.2). The CTL response in the 125 mcg dose group (n=9) was pre vs. max (0.8±0.2% vs. 1.8±0.3%; p=0.04), pre vs. post (0.8±0.2% vs. 0.6±0.2%; p=0.5), and pre vs. long-term (0.8±0.2% vs. 1.4±0.3%; p=0.5) (FIG. 4b). Both the 250 mcg and 125 mcg groups of GM-CSF had significant increases in pre to maximum dimer response, and the 250 mcg group trended towards significance. This analysis may be confounded by the fact that 33% (3/9) of the patients from the 250 mcg group had pre-existing immunity, while 77.8% (7/9) patients from the 125 mcg group had pre-existing immunity.

Figure 4C:
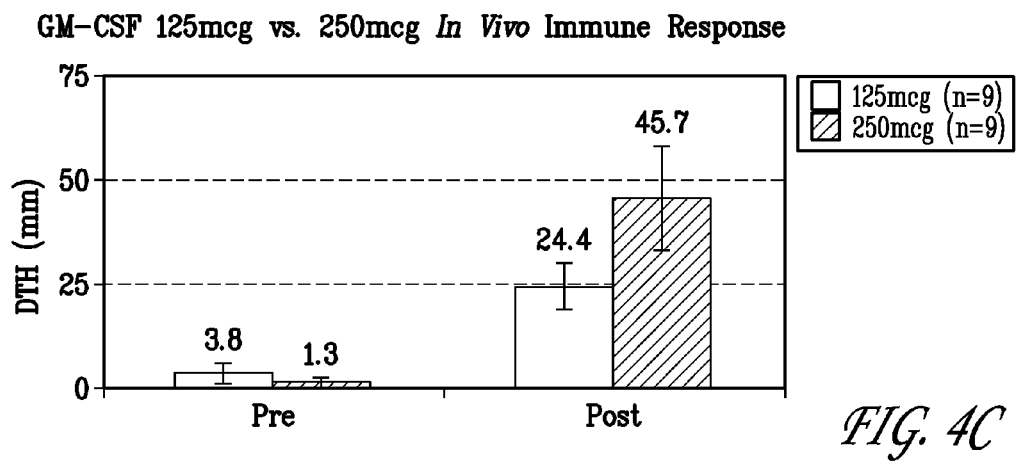

For in vivo immune responses, all patients, regardless of GM-CSF dose, had a statistically significant increase in DTH response comparing pre vs. post-vaccine measurements (125 mcg=3.8±2.5 mm to 24.4±5.5 mm; p=0.009, and 250 mcg=1.3±1.3 mm to 45.7±12.2 mm; p=0.008). Patients receiving 250 mcg of GM-CSF had a trend toward larger post-vaccine DTH responses, albeit not statistically significant (45.7±12.2 mm vs. 24.4±5.5 mm; p=0.1) (FIG. 4c).

HER2 Expression Status.

The in vivo immune response data for patients grouped according to level of HER2 expression (IHC 1+, IHC 2+, or IHC 3+) were analyzed, as shown in Table 2 below. All three groups mounted substantial DTH reactions post vaccine. Surprisingly, patients having low to intermediate expression of of HER2/neu mounted in vivo immune responses similar in magnitude to the post-vaccine DTH responses observed in IHC 3+ patients. The low to intermediate expressing of HER2/neu patients also showed a trend toward more statistically significant differences between pre and post-vaccine DTH responses as compared to the IHC 3+ patients. Specifically, IHC 2+ patients had a statistically significant increase in DTH response comparing pre vs. post-vaccine measurements (2.3±2.3 mm to 32.5±6.6 mm; p=0.02). Patients with IHC 1+ and IHC 3+ had a trend toward more potent post-vaccine DTH responses, with the IHC 1+ patients closer to statistical significance than the IHC 3+ patients (IHC 1+=2.1±2.1 mm to 33.0±12.8 mm; p=0.06, and IHC 3+=3.9±3.9 mm to 44.0±17.9 mm; p=0.1). When the DTH data of the low to intermediate expressing patients were combined ("LE") and compared to the DTH data from the IHC 3+ patients ("OE"), LE patients were unexpectedly observed to have a statistically significant increase in DTH response comparing pre vs. post-vaccine measurements (2.0±1.4 mm to 31.7±7.1 mm; p=0.002) as compared to the OE patients (3.9±3.9 mm to 44.0±17.9 mm; p=0.1).

TABLE 2

DTH Responses Based on HER2 Expression Level

|  | IHC 1+ | IHC 2+ | IHC 3+ | No IHC |
|---|---|---|---|---|
| Number GP2 pre-DTH | 7 | 5 | 5 | 1 |
| average ± SE | 2.1 ± 2.1 | 2.3 ± 2.3 | 3.9 ± 3.9 | |
| median (range) | 0 (0-14.5) | 0 (0-11.5) | 0 (0-19.5) | |
| GP2 post-DTH | | | | |
| average ± SE | 33.0 ± 12.8 | 32.5 ± 6.6 | 44.0 ± 17.9 | |
| median (range) | 23.5 (0-104) | 28 (22.5-58.5) | 30 (14.5-114.5) | |
| p-value pre-post (t-test) | 0.06 | 0.02 | 0.1 | |

|  | LE | OE |
|---|---|---|
| Number GP2 pre-DTH | 13 | 5 |
| average ± SE | 2.0 ± 1.4 | 3.9 ± 3.9 |
| median (range) | 0 (0-14.5) | 0 (0-19.5) |
| GP2 post-DTH | | |
| average ± SE | 31.7 ± 7.1 | 44.0 ± 17.9 |
| median (range) | 24.0 (0-104) | 30 (14.5-114.5) |
| p-value pre-post (t-test) | 0.002 | 0.1 |

Epitope Spreading.

Figure 5:
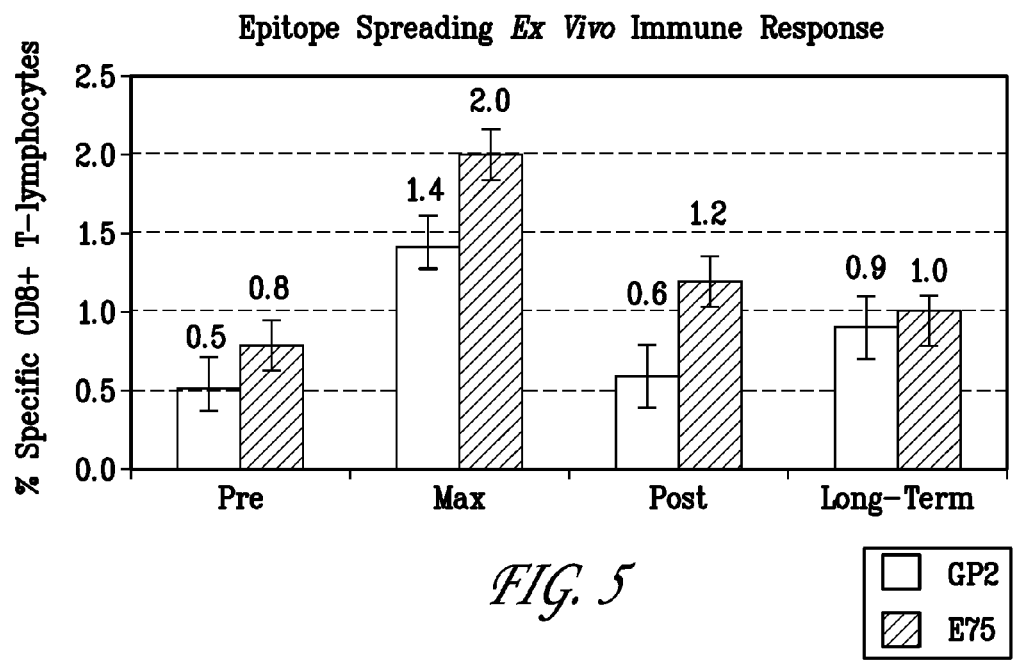
FIG. 5 shows ex vivo immune response and epitope spreading in response to GP2. Mean E75 specific $CD8^+$ T-lymphocytes were measured in response to vaccination with GP2 peptide vaccine. Pre-vaccination E75 dimer vs. maximum (0.8±0.2% vs. 2.0±0.2%, P=0.0001), pre vs. post (0.8±0.2% vs. 1.2±0.2%, p=0.1), and pre vs. long-term (0.8±0.2% vs. 1.0±0.2%; P=0.6) were compared. No statistical differences between GP2 and E75 values were noted, but a trend towards larger E75 maximum dimer response was noted (2.0±0.2% vs. 1.4±0.2%; P=0.07).

Lastly, evaluation for evidence of intra-antigenic epitope spreading in response to vaccination with GP2+GM-CSF was performed. Measurement of both GP2-specific and E75-specific CTLs before, during, and after vaccination was performed. We observed that the percentage of E75-specific CTLs did rise significantly when we compared pre vs. maximum levels (0.8±0.2% vs. 2.0±0.2%; p=0.0001), and increased, but not significantly, pre vs. post-vaccine (0.8±0.2% vs. 1.2±0.2%; p=0.1) and pre vs. long-term (0.8±0.2% vs. 1.0±0.2%; p=0.6) in response to vaccination with GP2-peptide (FIG. 5). Of note, these levels of E75-specific CTLs are similar in magnitude to primary vaccination with E75 with the only difference being a trend towards larger E75 maximum dimer responses compared to GP2 (2.0±0.2% vs. 1.4±0.2%; p=0.07).

The observation of more robust DTH and local reactions along with greater CTL responses amongst the patients starting with higher GM-CSF doses suggests that the immunoadjuvant dose plays a role in the immunogenicity, and possibly the efficacy of HER2/neu peptide vaccines. As previously reported, larger doses of E75+GM-CSF led to more robust DTH reactions and trends toward fewer recurrences with improved survival in the patients who did recur (Peoples G E et al., Clin Cancer Res (2008) 14(3):797-803). Another recent study with E75 has shown that administering E75 and GM-CSF in six monthly inoculations to disease-free, breast cancer patients in the optimal dose group (ODG) of 1000 mcg E75 and 250 mcg GM-CSF (1000:250:6) results in an average post-vaccination DTH response of 21.5 mm. Holmes et al., Cancer (2008) 113:1666-75. The post-vaccination responses of the suboptimal dose group (SDG) were significantly lower than the OBD. Interestingly, the patients in the ODG had fewer cases of disease recurrence despite having more aggressive disease, indicating that the DTH response provides a useful marker for clinical outcome and, in particular, for measuring predisposition to disease recurrence, with a lower DTH correlating with a higher predisposition to disease recurrence or a shorter disease-free survival time and vice versa.

Surprisingly, even though GP2 has a relatively poor binding affinity for HLA-A2 and is the subdominant epitope, patients treated with GP2 and GM-CSF exhibited markedly larger DTH responses as compared to those induced with the immunodominant epitope, E75 (plus GM-CSF). In this trial with GP2, larger DTH responses were seen in patients without pre-existing immunity (43.9 mm) as well as patients receiving the higher GM-CSF dose (45.7 mm). Specifically, the average post-vaccination DTH response for all GP2+GM-CSF patients was 35.1 mm, whereas the average post-vaccination DTH response for E75+GM-CSF patients was 11.3 mm (SDG) and 21.5 mm (ODG). Patients treated with GP2 and 250 mcg GM-CSF had an average post-vaccination DTH over twice the size of the similarly treated E75 OBD (1000:250:6) patients (45.7 mm vs. 21.5 mm). Surprisingly, in comparison to previous trials with the immunodominant peptide E75, the average DTH reaction to GP2 was approximately twice the size of that induced by E75 with on average half the peptide dose. Not only do these findings further illustrate the immunogenicity of GP2 and underscore its clinical relevance, but the in vivo DTH data also strongly suggest that GP2, despite being the subdominant epitope, should be more effective at reducing breast cancer recurrence than E75.

Example 2

Phase II Trial of GP2+GM-CSF

Methods

Disease-free, high risk breast cancer patients who have completed standard adjuvant therapy were enrolled at multiple sites and randomized to receive six monthly inoculations of either 500 mcg of GP2 with 125 mcg of GM-CSF (Peptide group; PG) or 125 mcg of GM-CSF alone (adjuvant group; AG). Toxicity was assessed after each inoculation. Immunologic response was monitored by measured delayed type hypersensitivity reactions (DTH) and an HLA-A2:Immunoglobulin dimer assay to detect GP2-specific CD8+ T-lymphocytes. Patients were monitored clinically, radiographically, and pathologically for recurrence.

Results

Thus far, 50 (27 PG, 23 AG) of the planned 200 patients have completed the primary series. The PG and AG have similar demographic/prognostic characteristics (Table 3).

TABLE 3

Patients demographics and prognostic characteristics for Phase II Study Demographics

|  | Peptide | Adjuvant | p = |
|---|---|---|---|
| N = | 27 | 23 |  |
| Age (median) | 52 | 51 | 0.88 |
| Node Positive | 51.9% | 69.6% | 0.32 |
| Grade 3 | 51.9% | 56.5% | 1 |
| Tumor >= 2 cm | 66.7% | 52.2% | 0.45 |
| ER/PR neg | 40.7% | 43.5% | 0.92 |
| HER2 overexpress | 59.3% | 47.8% | 0.6 |

Figure 6:
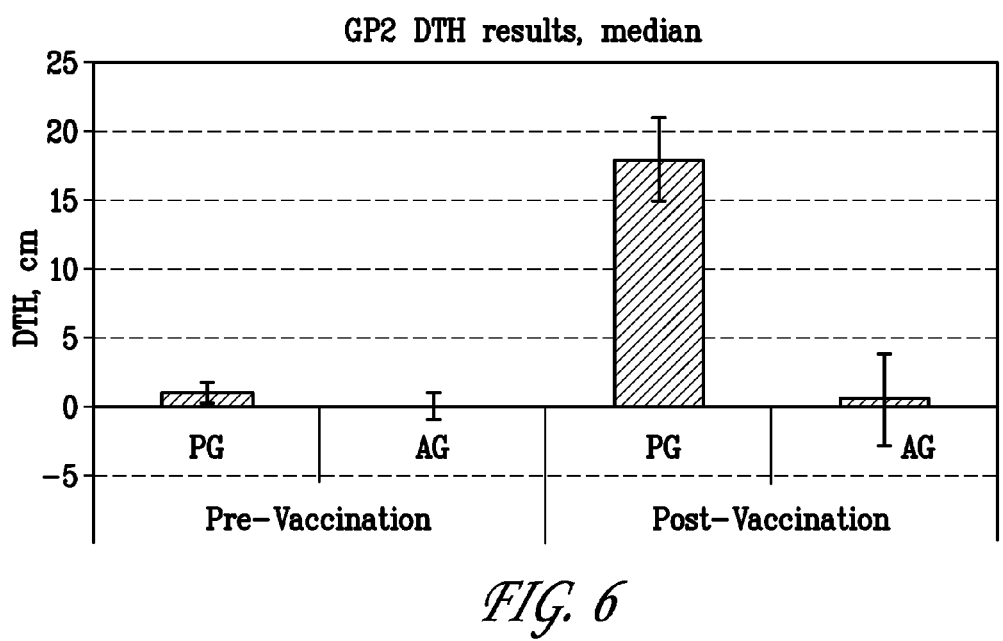
FIG. 6 shows the in vivo immune response of patients enrolled in GP2 phase II trial. Median DTH reaction to GP2 increased significantly from pre-vaccination level to post-vaccination level in the GP2 peptide group (PG) (1.0±0.8 cm to 18.0±3.1 cm; p<0.0001) and to a lesser extent in the control, adjuvant group (AG) (0.0±1.0 cm to 0.5±3.3 cm; p<0.01). The post-vaccination DTH was significantly larger in the PG compared to the AG (18.0±3.1 cm vs 0.5±3.3 cm, p=0.002).

Toxicity profiles in the PG and AG were nearly identical with no grade 4-5 local toxicities and no grade 3-5 systemic toxicities in either arm. Median DTH reaction to GP2 increased significantly from pre-vaccination level after completion of the primary series (post-vaccination) in the PG group (1.0±0.8 cm to 18.0±3.1 cm; p<0.0001) and to a lesser extent in the AG group (0.0±1.0 cm to 0.5±3.3 cm; p<0.01) (FIG. 6). The post-vaccination DTH was significantly larger in the PG compared to the AG (18.0±3.1 cm vs 0.5±3.3 cm, p=0.002) (FIG. 6). All (27/27) PG patients displayed significant immunity (SI) by DTH (reaction larger than 1 cm) post-vaccination compared to 45.5% (10/22) of AG patients. Of the 10 AG patients with post-vaccination SI, 50% (5/10) had pre-vaccination SI compared to just 16.6% (2/12) without SI post-vaccination (p=0.38). The % GP2-specific CD8+ lymphocytes significantly increased from baseline at 6 months after completion of the primary series in the PG (0.65±0.15 to 1.82±0.23, p=0.002) and did not change significantly in the AG (1.08±0.16 to 1.41±0.49, p=0.45).

Because this is an ongoing multi-site study, with patients enrolled on a rolling basis, recurrence data are not yet complete. However, the preliminary data show that the PG patients have experienced an approximately 50% reduction in recurrence rate as compared to the control AG patients, similar to recurrence rates observed at 24 months in patients treated with E75+GM-CSF (Peoples G E et al., Clin Cancer Res (2008) 14(3):797-803). More specifically, at a median follow up of 17.9 months, the recurrence rate in the PG is 7.4% (2/27) compared to 13% (3/23) in the AG (p=0.65). More recurrence rate data will become available as more patients undergo follow up at 24 months and beyond and as more patients enroll in the study.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed:

1. A method of preventing breast cancer recurrence in a subject, comprising:
   a) selecting the subject, wherein the subject is in remission following treatment with a standard course of therapy, and wherein the subject, prior to remission, had breast cancer cells with low or intermediate expression of HER2/neu, wherein low or intermediate expression of HER2/neu is an immunohistochemistry (INC) rating of 1+ or 2+ protein expression or a fluorescence in situ hybridization (FISH) rating of less than about 2.0 for HER2/neu gene expression; and
   b) administering to the subject selected in step a) a composition in an amount effective to prevent breast cancer recurrence,
   wherein the composition comprises a pharmaceutically effective carrier, a peptide consisting of the amino acid sequence SEQ ID NO: 2, and granulocyte macrophage-colony stimulating factor, and wherein, other than the peptide consisting of the amino acid sequence of SEQ ID NO: 2, the composition does not contain any other Her2/neu-derived peptides.

2. The method of claim 1 wherein the composition is administered by injection or inoculation.

3. The method of claim 2, wherein the injection is an intradermal injection.

4. The method of claim 2, wherein the composition is injected in one or more split doses.

5. The method of claim 4, wherein the injection sites on the subject are located about 5 cm apart from each other.

6. The method of claim 1, wherein the composition is administered every month for six months.

7. The method of claim 1, further comprising administering to the subject a booster comprising an effective amount of a vaccine booster composition comprising a pharmaceutically effective carrier and a peptide consisting of the amino acid sequence of SEQ ID NO: 2.

8. The method of claim 7, wherein the booster is administered every six or 12 months after a primary immunization schedule is completed.

9. The method of claim 1, wherein the subject is a human.

10. The method of claim 9, wherein the human expresses human leukocyte antigen A2.

11. The method of claim 9, wherein cancer cells from the human express detectable levels of HER2/neu.

12. The method of claim 1, wherein the granulocyte macrophage-colony stimulating factor is recombinant human granulocyte macrophage-colony stimulating factor.

13. The method of claim 8, wherein the vaccine booster composition further comprises an adjuvant.

14. The method of claim 13, wherein the adjuvant is granulocyte macrophage-colony stimulating factor.

15. The method of claim 1, wherein administering the composition induces a cytotoxic T-lymphocyte response to the peptide consisting of the amino acid sequence SEQ ID NO: 2.

16. The method of claim 1, wherein the subject does not have pre-existing immunity to the peptide consisting of the amino acid sequence of SEQ ID NO: 2.

* * * * *